United States Patent
Zhang et al.

(10) Patent No.: US 12,098,367 B2
(45) Date of Patent: Sep. 24, 2024

(54) ARGONAUTE PROTEIN MUTANT AND USE THEREOF

(71) Applicant: BERRY GENOMICS CO., LTD, Beijing (CN)

(72) Inventors: Jianguang Zhang, Beijing (CN); Aiping Mao, Beijing (CN)

(73) Assignee: BERRY GENOMICS CO., LTD., Beijing (CN)

( * ) Notice: Subject to any disclaimer, the term of this patent is extended or adjusted under 35 U.S.C. 154(b) by 1049 days.

(21) Appl. No.: 16/978,428

(22) PCT Filed: Jan. 3, 2019

(86) PCT No.: PCT/CN2019/070253
§ 371 (c)(1),
(2) Date: Sep. 4, 2020

(87) PCT Pub. No.: WO2019/169945
PCT Pub. Date: Sep. 12, 2019

(65) Prior Publication Data
US 2021/0332353 A1  Oct. 28, 2021

(30) Foreign Application Priority Data

Mar. 6, 2018  (CN) .......................... 201810184689.6
Dec. 10, 2018  (CN) .......................... 201811505553.7

(51) Int. Cl.
*C12N 15/10* (2006.01)
*C07K 14/195* (2006.01)
*C12N 9/22* (2006.01)

(52) U.S. Cl.
CPC ........ *C12N 15/1093* (2013.01); *C07K 14/195* (2013.01); *C12N 9/22* (2013.01); *C07K 2319/85* (2013.01)

(58) Field of Classification Search
None
See application file for complete search history.

(56) References Cited

U.S. PATENT DOCUMENTS

2006/0141600 A1  6/2006  Joshua-Tor et al.

FOREIGN PATENT DOCUMENTS

| CN | 108048532 | 5/2018 |
| WO | WO 2015/157534 | 10/2015 |
| WO | WO 2018/011236 | 1/2018 |

OTHER PUBLICATIONS

NCBI Reference Sequence WP_011011654.1 Sep. 1, 2023.*
Definition of kit: Merriam-Webster Dictionary. Kit Definition & Meaning—Merriam-Webster. Retrieved Nov. 13, 2023.*
Olovnikov, et al. "Bacterial Argonaute Samples the Transcriptome to Identify Foreign DNA" Molec. Cell 51 (2013) pp. 594-605.
EPO. "Extended European Search Report" 19763666.5 (Oct. 18, 2021) pp. 1-7.
PCT International Search Report (w/ English Translation) and Written Opinion for corresponding PCT Application No. PCT/CN2019/070253 dated, Mar. 22, 2019—12 pages.
Wang et al. "Nucleation, Propagation and Cleavage of Target RNAs in Ago Silencing Complexes," Nature, vol. 461, Oct. 8, 2009, pp. 754-761.
Garcia-Garcia et al. "Assessment of the Latest NGS Enrichment Capture Methods in Clinical Context," Sci Rep 6, Feb. 11, 2016—8 pages.
Bodi et al., Comparison of Commercially Available Target Enrichment Methods for Next-Generation Seguencing, J. Biomol Tech, vol. 24, Issue 2, Jul. 2013, pp. 73-86.
Newman et al. "Integrated Digital Error Suppression for Improved Detection of Circulating Tumor DNA," Nature Biotechnology, vol. 34, No. 5, May 2016, pp. 547-560.
Samorodnisky et al., "Evaluation of Hybridization Capture Versus Amplicon-Based Methods for Whole-Exome Sequencing," Human Mutation, vol. 36, No. 9, Jun. 2015, pp. 903-914.
Kuscu et al., "Genome-wide analysis reveals characteristics of off-target sites bound by the Cas9 endonuciease," Nature Biotechnology, Vo. 32, No. 7, Jul. 2014—pp. 677-683.
Wu et al., "Genome-wide binding of the CRISPR endonuclease Cas9 in mammalian cells," Nature Biotechnolgy, vol. 32, No. 7, Jul. 2014, pp. 670-676.
Liu et al., "In Situ Capture of Chromatin Interactions by Biotinylated dCas9," Cell 170, Aug. 24, 2017, pp. 1028-1043.

(Continued)

*Primary Examiner* — Oluwatosin A Ogunbiyi

(74) *Attorney, Agent, or Firm* — Dority & Manning, P.A.

(57) ABSTRACT

The present invention relates to a mutant of Argonaute protein lacking a DNA cleavage activity but having a DNA binding activity, wherein the mutation of the mutant is located in a PIWI domain. The present invention also relates to a use based on the protein mutant, especially in enrichment of a target DNA and construction of sequence libraries. Therefore, the present invention also relates to a method for enrichment of a target DNA, comprising the following steps: (a) designing a guide sequence for a specific sequence in the target DNA; (b) binding the mutant according to the present invention, the guide sequence and the target DNA to obtain a mutant-guide sequence-target DNA ternary complex; (c) capturing the mutant-guide sequence-target DNA ternary complex through a capture medium; and (d) separating the target DNA from the captured mutant-guide sequence-target DNA ternary complex to obtain an enriched target DNA.

15 Claims, 7 Drawing Sheets

Specification includes a Sequence Listing.

(56) References Cited

OTHER PUBLICATIONS

Fujita et al., Efficient sequence-specific isolation of DNA fragments and chromatin by in vitro enChIP technology using recombination CRISPR ribonucleoproteins, Genes to Cells (2016) 21, pp. 370-377.
Swarts et al., "The evolutionary journey of Argonaute proteins," Nat Struct Mol Biol, vol. 21, No. 9, Sep. 2014, pp. 743-753.
Song et al., "Crystal Structure of Argonaute and Its Implications for RISC Slicer Activity," Science, vol. 305, Sep. 3, 2004, pp. 1434-1437.
Swarts et al. "Argonaute of the archaeon Pyrococcus furious is a DNA-guided nuclease that targets cognate DNA," Nucleic Acids Research, vol. 43, No. 10, Apr. 2015, pp. 5120-5129.
Raines et al, "The S•Tag Fusion System for Protein Purification," Methods Enzymology, vol. 326, 2000, pp. 362-376.
CNIPA. "Notice of First Opinion" 201811505553.7 (Mar. 16, 2022) pp. 1-7. (Translation not available, reference designation provided on p. 6-7).

\* cited by examiner

MKAKVVINLVKINKKIIPDKIYVYRLFNDPEEELQKEGYSIYRLAYENVGIVIDPEN
LIIATTKELEYEGEFIPEGEISFSELRNDYQSKLVLRLLKENGIGEYELSKLLRKFR
KPKTFGDYKVIPSVEMSVIKHDEDFYLVIHIIHQIQSMKTLWELVNKDPKELEEFLM
THKENLMLKDIASPLKTVYKPCFEEYTKKPKLDHNQEIVKYWYNYHIERYWNTPEAK
LEFYRKFGQVDLKQFATLAKFASKIKFNKNYKIVLLPQLVVPTYNAEQLESDVAKEI
LEYTKLMPEERKELLENILAEVDSDIIDKSLSEIEVEKTAQELENKTRVRDDKGNSV
PISQLNVQKSQLLLWTNYSRKYPVILFYEVPEKFRKIREIPMFIILDSGLLADIQNF
ATNEFRELVKSMYYSLAKKYNSLARKARSTNEIGLFFLDFRGKEKVITEDLNSDKGI
IEVVEQVSSFMKGKELGLAFIAARNKLSSEKFEEIKRRLFNLNVISQVVNEDTLKNK
RDKYDRNRLDLFVRENLLFQVLSKLGVKYYVLDYRFNYDYIIGIDVAFMKRSEGYIG
GSAVMFDSQGYIRKIVPIKIGEQRGESVDNNEFFKEMVDKFKEFNIKLDNKKILLLR
DGRITNNEEEGLKYISEMFDIEVVTMDYIKNHFVRAFANMKMYFNLGGAIYLIPHKL
KQAKGTPIPIKLAKKRIIKNGKVEKQSITRQDVLDIFILTRLNYGSISADMRLPAPV
HYAHKFANAIRNEWKIKEEFLAEGFLYFV (SEQ ID NO: 1)

Fig 2

MNHLGKTEVFLNRFALRPLNPEELRPWRLEVVLDPPPGREEVYPLLAQVARRAGGVT
VRMGDGLASWSPPEVLVLEGTLARMGQTYAYRLYPKGRRPLDPKDPGERSVLSALAR
RLLQERLRRLEGVWVEGLAVYEREHARGPGWRVLGGAVLDLNVSDSGAFLLEVDPAY
RILCEMSLEAWLAQGHPLFKRVRNAYDRRTWELLRLGEEDPKELPLPGGLSLLDYHA
SKGRLQGREGGRVAWVADPKDPRKPIPHLTGLLVPVLTLEDLHEEEGSLALSLPWEE
RRRTREIASWIGRRLGLGTPEAVRAQAYRLSIPKLMGRRAVSKPADALRVGFYRAQ
ETALALLRLDGAQGWPEFLRPALLRAFGASGASLRLHTLHAHPSQGLAFREALRKAK
EEGVQAVLVLTPPMAWEDRNRLKALLLREGLPSQILNVPLREEERHRWENALLGLLA
KAGLQVVALSGAYPAELAVGFDAGGRESFRFGGAACAVGGDGGHLLWTLPEAQAGER
IPQEVVWDLLEETLWAFRRKAGRLFSRVLLLRDGRVPQDEFALALEALAREGIAYDL
VSVRKSGGGRVYPVQGRLALGLYVPLEDKTFLLLTVHRDFRGTPRPLKLVHEAGDTP
LEALAHQIFHLTRLYPASGFAFPRLPAPLHLADRLVKEVGRLGIRHLKEVDREKLFF
V (SEQ ID NO: 2)

Fig 3

MVLNKVTYKINAYKIKEEFIPKEVHFYRIKSFVNEAFNFYRFVNFYGGMIINKKDKS
FVLPYKVDNKVLKYKDGNNEIPIDIEYIKSLKLEYVKPEIAEKLVRGYLKSVHKIEP
ELSRTIKNIRKHKVVENIKVESYCEYEVKKHDGDYYLILNFRHTASITKHLWDFVNR
DKALLEEYVGKKIIFKPNPKVRYTISLVDAPNPQKIEEIMSHITKYYKWSEDMVKST
FGEIDYNQPIMYCEEILEPFAPQFCNLVFYMDELDSYILKELQSYWRLSNENKGKII
NETAKKLRFIDNTPKELEFMKFNNTPLLVKDVNKNPTKIYSTNTLFTWIYNQNAKIY
LPYDVPEIIRNKNLLTYILIDEEIKDELKAIKDKVNKMFRNYNKIANKTELPKFNYA
NRWKYFSTDDIRGIIKEIKSEFNDEICFALIIGKEKYKDNDYYEILKKQLEDLKIIS
QNILWENWRKDDKGYMTNNLLIQIMGKLGIKYFILDSKTPYDYIMGLDTGLGLFGNH
RVGGCTVVYDSEGKIRRIQFIETPAFGERLHLPYVIEYLENKANIDMENKNILFLRD
GFIQNSEFNDLKEISKELNSNIEVISIRKNNKYKVFTSDYRIGSVFGNDGIFLPHKT
PFGSNPVKLSTWLRFNCGNEEGLKINESIMQLLYDLTKMNYSALYGEGRYLRIPAFI
HYADKFVKALGKNWKIDEELLKHGFLYFI (SEQ ID NO: 3)

Fig 4

MYLNLYKIDIPKKIKELYFYNPDMEPKLFARNLSRVNNFKFQDSNDLVWIEIPDIDP
QITPKNVFQYKVEKEEIIKEEEDKKLFVKTLYKYIKKLFLDNDFYFKKGNNFISNSE
VFSLDSNENVNAHLTYKIKIHNISNEYYLSILPKFTFLSKEPALESAIKSGYLYNIK
SGKSFPYISGLDGILKIDIGNNQIVEVAYPENYLFNFTTRDAEKYGFSKEVHEIYKN
KVFEGFKKIPKTLGFLNKITNLNENYQLKDGYKIFINVIYKFKNGRSRYAKDVFKYS
FYKNEQPLKAIFFFSSKKQFFEVQKSLKELFHNKHSVFYRAAAELGFSKVEFLRDSK
TKSSAFLYNPEEFTVKNTEFINQIEDNVMAIVLLDKYIGNIDPLVRNFPDNLILQFI
LKEKLEDIKPFIIKSYVYKMGNFIPECKPFILKKMEDKEKNLYIGIDLSHDTYAFKT
NLCIAAVDNTGDILYIGKHKNLELNEKMNLDILEKEYIKAFEKYIEKFNVSPENVFI
LRDGRFIEDIEIIKNFISYNDTKYTLVEVNKNTNINSYDDLKEWIIKLDENTYIYF
KTFLNQKGVEVKILENNTDYTIEEIIEQIYLLTRVAHSTPYTNYKLPYPLHIANKVA
LTDYEWKLYIFY (SEQ ID NO:4)

Fig 5

MKLNLFEIMVPGKVKRIYYYNPQTPPEIFAKNLPRINNTIRFNDSSDLVWVELPFLQV
QILPEQAVVYKKREEVIESDEKLFIRTLYSYIKKLFKDNDFIATRQNLYISNRTKIP
FQNNKEVSWPESYQVKIYKIYEKYYLSINPRFTFLSTKPALESQVRSAYLLNTKSGK
SFPFVSAEDGKLVIAIDERTHKEVTHPENYFFNFTSKEAEELGVSKQIYEIYNNKLP
YLVEKISTELSFLKDLVNLNQYYEVKPDHQERITAFYKFANGNSDDIKKIFQLQPLK
SPGTLKMTFLFSSKYKNENISEPVRKVFASSDSAYRKALSELGLEIEYLRNPQTNKA
IFYYKEKTFEIENKEVLSSSGKIYAIVLLDEPQESLDNLIKNAPKNVVILPVLTPKI
ISDQIYILKSFAYKIVNFSQDAQTYQLLGLSDNALYIGFDLSHLFQKRVSHYAISAV
DRNSKVLYINQERDMPLNEKFELELLQKDIVKSIDRYKSVVKKPPNMIFLMRDGVFF
EDINLLKNYLDLLKIDYTIIEIDKNSNINSKQNLKGMIVKFEPNKYVYFAQTYNLQK
AVEINIVINNSKLSDEQIARETYLTTRLFHSTPYTNLKLPYFLYITDKVALLNNEWK
LYIPYFCDKI (SEQ ID NO:5)

Fig 6

MAPVQAADEMYDSNPHFDERQLVSNGFEVNLPDQVEVIVRLLPDPSKVKEERTRIMG
YWFVHWFDGKLFHLRIKAGGPNVDGEHRAIRTAEHPWLLRARLDDALEEALPKYAAV
KKRPFTPLAQKDELIDAAATAAGLSHRLLNSFKVIPRFALSPKIYEPVDGTTRVGVF
VTIGMRYDIEASLRDLLEAGIDLRGMYVVRKRQPGERGLLGRVRAISDDMVQLFEE
TDLASVNVNDAKLEGSKENFTBCLSALLGHNYKKLLNALDDQEAGYRTGPRFDDAVR
RMGEFLAKKPTRLADNINAQVGDRIVFSNEGQARNVRLAPKVEYVFDRTGAKSAEYA
WRGLSQFGPFDRPSFANRSPRILVYFSSTQGKVENFLSAFRDGMGSNYSGFSKGFV
DLMGLTKVEFVMCPVEVSSADENGAHTKYNSAIEDKLAGAGEVHAGIVVLFEDHARL
PDDENPYIHTKSLLLTLGVPTQQVRMPTVLLEPKSLQYTLQNFSIATYAKLNGTFWT
VNHDKAINDELVVGMGLAELSGSRTEKRQRFVGITTVFAGDGSYLLGNVSKECEYEG
YSDAIRESMTGILRELKKRNNWRPGDTVRVVFHAHRPLKRVDVASIVFECTBEIGSD
QNIQMAFVTVSHDHPFVLIDRSERGLEAYKGSTARKGVFAPPRGAISRVGRLTRLLA
VNSPQLIKRANTPLPTPLLVSLHPDSTFKDVDYLAEQALKFTSLSWRSTLPAATPVT
IFYSERIAELLGRLKSIFNWSSANLNIKLKWSRWFL (SEQ ID NO:6)

Fig 7

MGKEALLNLYRIEYRPKDTTFTVFKPTHEIQKEKLNKVRWRVFLQTGLPTFRREDEF
WCAGKVEKDTLYLTLSNGEIVELKRVGEEEFRGFQNERECQELFRDFLTKTKVKDKF
ISDFYKKFRDKITVQGKNRKIALIPEVNEKVLKSEEGYFLLHLDLKFRIQPFETLQT
LLEBNDFNPKRIRVKPIGIDFVGRVQDVFKAKEKGEEFFRLCMERSTHKSSKKAWEE
LLKNRELREKAFLVVLEKGYTYPATILKPVLTYENLEDEERNEVADIVRMEPGKRLN
LIRYILRRYVKALRDYGWYISPEEERAKGKLNFKDTVLDAKGKNTKVTTNLRKFLEL
CRPFVKKDVLSVEIISVSVYKKLEWRKEEPLKELINPLKNGIKLKIKGKSLTILAQT
REEAKEKLTPVINKIKDVDLVIVELEEYPKVDPYKSFLLYDFVKRELLKKMIPSQVI
LNRTLKNENLKFVLLNVAEQVLAKTGNIPYKLKEIEGKVDAFVGIDISRITRDGKTV
NAVAFTKIFNSKGELVRYYLTSYPAFGEKLTEKAIGDVFSLLEKLGFKKGSKIVVHR
DGRLYRDEVAAFKKYGELYGYSLELLEIIKRNNPRFFSNEKFIKGYFYKLSEDSVIL
ATYNQVYEGTHQPIKVRKVYGELPVEVLCSQILSLTLMNYSSFQPIKLPATVHYSDK
ITKLMLRGIEPIKKEGDIMYWL (SEQ ID NO:7)

Fig 8

MMEYKIVENGLTYRIGNGASVFISNTGELIKGLENYGPYEVFSLKYNQIALIHNNQF
SSLINQLKSQISSKIDEVWHIHNINISEFIYDSPHFDSIKSQVDNAIDTGVDGIMLV
LFEYNTPLYYKLKSYLINSIPSQFMRYDILSNRNLTFYVDNLLVQFVSKLGGKFWIL
NVDPEKGSDIIIGTGATRIDNVNLFCFAMVFKKDGTMLNNEISPIVTSSEYLTYLKS
TIKKVVYGFKKSNPDWDVEKLTLHVSGKRFKMKDGETKILKETVEELKKQEMVSRDV
KYAILHLNETHPFWMGDPNNRFHPYEGTKVKLSSKRYLLTLLQPYLKRNGLEMVTP
IKFLSVEIVSDNWTSEEYYHNVHEILDEIYYLSKMNWRGFFSRNLFVTVNYPKLVAG
IIANVNRYGGYPINPEGNRSLQTNPWFL (SEQ ID NO:8)

Fig 9

|  | D | E | D | X |
|---|---|---|---|---|
| hAgo2 | IFLGADVTHPP | QHRQEIIQDL | IIFYRDGVSEG | PAYYAHLVAFR |
| TtAgo | LAVGFDAGGRE | -GERIPQEVV | VLLLRDGRV-- | PLHLADSLVRE |
| MjAgo | YIMCLDTGLGI | -GERLHLPYV | ILFLRDGFI-- | PIHYADKFVKA |
| PfAgo | YIIGIDVAPMK | GEQRGESVDM | ILLLRDGRI-- | PVHYAHKFANA |
| MpAgo | LYIGIDLSHDT | -NEKMNLDIL | VFILRDGRPIE | PLHIANKVALT |
| TpAgo | LYIGFDLSHDF | -NEKFELELL | IFLMRDGVFFE | PLYITDKVALL |
| AaAgo | AFVGIDISRIT | -NENLKFVLL | IVVHRDGRLYR | TVHYSDKITKL |
| AfAgo | WILNVDPEKGS | -SQFMRYDIL | MVFKKDGTMLW | PLYYKLSYLI |
| RsAgo | LVVGMGLAELS | -NTFLPTFLL | TVFAGDGSYLL | NPYIHTKSLLL |

Fig 10

ARGONAUTE PROTEIN MUTANT AND USE THEREOF

TECHNICAL FIELD

The present invention relates to a mutant based on wild-type Argonaute protein (Ago) which lacks a DNA cleavage activity but has a DNA binding activity, and the use based on the protein mutant, especially in enrichment of a target DNA and construction of sequencing libraries. The invention also relates to a kit comprising the protein mutant.

SEQUENCE LISTING

A Sequence Listing has been filed electronically in ASCII format and is hereby incorporated by reference in its entirety. Said ASCII copy, created on Dec. 11, 2020, is named KING-30-WO-US_Sequence_List.txt and is 56,557 bytes in size.

BACKGROUND OF THE INVENTION

Highly efficient enrichment of target region DNA can effectively reduce sequencing cost and increase sequencing depth. For applications that normally require high-depth sequencing, such as somatic mutation detection, the enrichment performance of the target region is the main factor to determine its sensitivity and specificity[1].

At present, the mainstream enrichment methods for target region mainly include (1) a multiple primer amplification and (2) a capture method based on the nucleic acid probe hybridization[2]. (1) A target region enrichment method based on multiple primer amplification utilizes tens to thousands of pairs of primer simultaneously to amplify target sequences in template DNA in the same reaction system containing amplification enzyme, thereby realizing the purpose of target DNA enrichment. However, the interaction between primers and sequence differences between target sequences (such as GC content, ability to form secondary structures, and the like) will seriously affect the amplification efficiency, uniformity and specificity of target sequences. Therefore, with the increase of the target region, the design difficulty of multiple primer amplification increases rapidly, and the enrichment efficiency usually decreases correspondingly. In addition, the commonly used multiple primer amplification methods use face-to-face primer design, and both ends of the target fragment to be enriched need to be known sequences, which cannot realize enrichment of target sequences (such as gene fusion sequences) whose terminal sequences may be unknown. Thirdly, primer amplification requires primer pairs targeting both ends of the template DNA fragment simultaneously to realize the amplification. Thus, for highly fragmented DNAs (such as free DNAs), the utilization rate of primer amplification on the template DNA is very limited. (2) Capture method based on the nucleic acid probe hybridization uses single-stranded nucleic acid probe (80-120 nt) with a molecular tag (such as a biotin tag) to hybridize with target DNA fragments in hybridization buffer solution under high temperature condition for a long time (4-12 hours), and then the enrichment of target DNA is realized by capturing a probe hybridized with DNAs and having the molecular tag. The whole method has high requirements on the stability and persistence of reaction conditions and temperature and has a long process and a complicated operation. Some studies have pointed out that in the hybridization process, the reaction system will cause a DNA damage, and a mutation will be introduced 3. Meanwhile, the probe sequence is generally longer, which is difficult to synthesize and causes a higher cost. Meanwhile, in order to be enriched, the target sequence also needs a corresponding longer matching sequence to be paired with. Therefore, the capture efficiency of capture method based on the nucleic acid probe is often poor for shorter DNAs (such as free DNAs)[4].

To sum up, the method based on multiple primer amplification is difficult to effectively enrich the target region in fairly large range and cannot effectively enrich the fused gene DNAs. Although the capture method based on the nucleic acid probe hybridization overcomes many limitations caused by the multiple primer amplification, the operation is complicated and takes a long time, and the capture efficiency for short fragments is poor.

In recent years, researchers have found that some programmable DNA binding proteins can bind to the target DNA faster and more specifically than the nucleic acid probe hybridization. For example, in the Clustered Regularly Interspaced Short Palindromic Repeats (CRISPR)-Cas (CRISPR-associated Protein) system, Cas proteins encoded by Cas gene can specifically bind to target dsDNA sequence under the guidance of a segment of RNA, and then the sequence is excised. Researchers has further found that mutation of certain specific functional sites of wild-type Cas protein (e.g., Cas9 protein) can make it lose its cleavage activity to target DNAs, but retain the activity of binding to the target DNA according to sgRNA guide probes[5,6]. The Cas9 protein mutant (dCas9) thus obtained can rapidly and efficiently capture the target DNAs[7,8].

However, use of dCas9 to capture the target DNA still has the following disadvantages: (1) The recognition sequence of dCas9 needs to contain a protospacer adjacent motif (PAM) usually consisting of three bases NGG (N represents any base) at the 3' end. Therefore, the target DNA that dCas9 can capture is not any sequence[5, 6]. (2) The guide RNA required for dCas9 is usually has a length of close to 100 nucleotides, and such long RNA sequence is relatively difficult to be synthesized[5,6]. (3) When the guide RNA required for dCas9 is expressed through plasmids or transcribed in vitro, it takes a long time and is complicated to operate, and simultaneously brings problems of unstable expression and contamination. Moreover, an RNA is easy to form secondary structure, leading to failure. (4) dCas9 has a serious off-target effect, because the recognition specificity on the target site depends on the pairing of gRNAs with 10-12 bp bases near PAM, while the mismatch of 8-10 bp bases away from PAM has no obvious influence on the recognition of target sites. It will greatly affect the capture efficiency of dCas9 on the target DNA.

Therefore, there is a need for a new method that can overcome the above disadvantages of dCas9 and capture the target DNA efficiently and accurately.

SUMMARY OF THE INVENTION

The present invention provides an isolated Argonaute (Ago) protein mutant, which has a DNA binding activity but lacks a DNA cleavage activity, thus being capable to be used for enrichment of the target DNA in an easy-to-operate, efficient and accurate manner, and thereby solving the problems of a limited target DNA range, a long time consumption, a complex operation, a poor efficiency and a serious off-target when using the existing technologies (in particular, the hybridization capture method based on nucleic acid probe and the capture method based on dCas9) to enrich the target DNA sequence.

Therefore, in a first aspect, the present invention provides an isolated mutant of Ago protein having a DNA binding activity but lacking a DNA cleavage activity.

Ago protein is widely found in eukaryotes and prokaryotes and is a protein with ribonuclease function under the guidance of RNAs or DNAs. Eukaryotic Ago proteins are key proteins of RNA interference (RNAi) mechanism. They perform a specific splicing function by binding to 5' phosphorylated small RNAs with a length of 20-30 bases[9]. Eukaryotic Ago proteins can form an RNA-induced silencing complex (RISC) with a series of auxiliary proteins[9,10], which can induce gene silencing after transcription by making mRNA unstable or by translation inhibition, thus playing an important role in various biological activities such as embryo development, cell differentiation, stem cell maintenance and transposon silencing. Unlike the eukaryotic Ago proteins, a prokaryotic Ago protein usually lacks the auxiliary protein bound with to perform RNAi function[9]. However, some prokaryotic Ago proteins can also specifically cleave RNAs or DNAs using small RNAs or DNAs as a guide sequence[9,10].

Ago protein is a multi-domain protein, including N-terminal domain, PAZ domain, MID domain and PIWI domain[9]. Prokaryotic Ago protein has a two-leaf structure, in which MID domain and PIWI domain form one leaf, while N-terminal domain and PAZ domain form another leaf. In general, the PAZ domain is bound to the 3' end of the guide sequence, and the MID domain is used to recognize the 5' end of the guide sequence. The PIWI domain can perform an endonuclease function similar to RNAse to cleave the target DNAs due to RNase H-like folding[9]. In the PIWI domain, the catalytic site responsible for RNaseH enzyme activity includes an aspartic acid-aspartic acid-histidine/lysine motif bound to divalent metal ions, and glutamic acid (E) located in a structural subdomain called "glutamic acid finger". These four amino acids and their adjacent sequences constitute DEDX structural region and become the key feature of PIWI domain of Ago protein[9]. Although the whole sequences of Ago proteins in different species are significantly different, the DEDX structural region in PIWI domain has a higher conservativeness (FIG. 1)[9,11].

As used herein, the term "mutant of Ago protein" or "dAgo" can be used interchangeably and refers to Ago protein obtained by mutation, which has a DNA binding activity but lacks a DNA cleavage activity. In the present invention, Ago protein is derived from prokaryotes, such as bacteria or archaea. Examples of bacteria include, for example, *Marinitoga, Thermotoga, Rhodobacter*, and *Aquifex*. Examples of archaea include, for example, *Pyrococcus, Methanocaldococus, Thermus*, and *Archaeoglobus*.

In a specific embodiment, Ago protein is derived from prokaryotes selected from the group consisting of *Pyrococcus furiosus, Thermus thermophilus, Methanocaldococus jannaschii, Marinitoga piezophila, Thermotoga profunda, Rhodobacter sphaeroides, Aquifex aeolicus* and *Archaeoblobus fulgidus*.

More preferably, the amino acid sequence of the Ago protein is selected from SEQ ID NOs: 1-8.

As used herein, the term "mutation" refers to a change in a given amino acid residue in a protein, such as insertion, deletion, or substitution of an amino acid. "Deletion" refers to the lack of one or more amino acids in a protein. "Insertion" refers to the increase of one or more amino acids in a protein. "Substitution" refers to the replacement of one or more amino acids with another amino acid residue in a protein. Mutation methods of proteins are known in the art, for example, corresponding coding sequences of proteins can be mutated by a site-directed mutagenesis.

In one embodiment, the Ago protein mutant has a mutation in the PIWI domain, and the mutation results in lack of the DNA cleavage activity. Preferably, the mutation comprises one or more mutations at the following positions:
  substitution of amino acid residues at positions 558, 596, 628 and 745 of SEQ ID NO: 1, and of amino acid residues at the positions corresponding to the above positions, or
  deletion of amino acid at positions 628-770 of SEQ ID NO. 1, and of amino acid residues at the position corresponding to the above positions. Preferably, the substitution means that the corresponding amino acid is substituted by alanine or glutamic acid.

As used herein, the term "amino acids at corresponding positions" refers to the amino acid residues in a sequence corresponding to a given position in a reference sequence when two sequences are in the best alignment. Those skilled in the art are aware of methods for determining the amino acid position in the sequence corresponding to the given position in the reference sequence. In the present invention, the reference sequence could be, for example, SEQ ID NO: 1.

In SEQ ID NO: 2, amino acid residues at positions 478, 512, 546 and 660 correspond to amino acid residues at positions 558, 596, 628 and 745 of SEQ ID NO: 1, respectively; and the amino acid residues at positions 546 to 685 correspond to amino acid residues at positions 628 to 770 of SEQ ID NO: 1.

In SEQ ID NO: 3, amino acid residues at positions 504, 541, 570 and 688 correspond to amino acid residues at positions 558, 596, 628 and 745 of SEQ ID NO. 1, respectively; and the amino acid residues at positions 570 to 713 correspond to amino acid residues at positions 628 to 770 of SEQ ID NO: 1.

In SEQ ID NO: 4, amino acid residues at positions 446, 482, 516 and 624 correspond to amino acid residues at positions 558, 596, 628 and 745 of SEQ ID NO: 1, respectively; and the amino acid residues at positions 516 to 639 correspond to amino acid residues at positions 628 to 770 of SEQ ID NO: 1.

In SEQ ID NO: 5, amino acid residues at positions 439, 475, 509 and 617 correspond to amino acid residues at positions 558, 596, 628 and 745 of SEQ ID NO: 1, respectively; and the amino acid residues at positions 509 to 637 correspond to amino acid residues at positions 628 to 770 of SEQ ID NO: 1.

In SEQ ID NO: 6, amino acid residue at position 554 corresponds to amino acid residue at position 628 of SEQ ID NO: 1; and the amino acid residues at positions 554 to 777 correspond to amino acid residues at positions 628 to 770 of SEQ ID NO: 1.

In SEQ ID NO: 7, amino acid residues at position 502, 464, 571 and 683 correspond to amino acid residues at positions 558, 596, 628 and 745 of SEQ ID NO: 1, respectively; and the amino acid residues at positions 571 to 706 correspond to amino acid residues at positions 628 to 770 of SEQ ID NO: 1.

In SEQ ID NO: 8, amino acid residues at positions 174 and 205 correspond to amino acid residues at positions 558 and 628 of SEQ ID NO: 1 respectively; and the amino acid residues at positions 205 to 427 correspond to amino acid residues at positions 628 to 770 of SEQ ID NO: 1.

Optionally, the Ago protein mutant can also comprise mutations in the following domains: N-terminal domain, and PAZ domain. In this embodiment, the mutation of the Ago protein mutant in the N-terminal domain and/or PAZ domain can be a functionally conservative mutation or a mutation that does not affect the binding activity of the Ago protein.

As used herein, the term "functionally conservative mutation" refers to a mutation that does not change the overall structure and function of a protein. Examples of conservative mutations include mutation of one nonpolar (hydrophobic) residue such as isoleucine, valine, leucine or methionine into another nonpolar residue; mutation of one polar (hydrophilic) residue into another polar residue, such as mutation between arginine and lysine, glutamine and asparagine, glycine and serine; mutation of one basic residue such as lysine, arginine and histidine into another basic residue; or mutation of one acidic residue such as aspartic acid and glutamic acid into another acidic residue.

In one embodiment, the Ago protein mutant carries a specific tag, preferably a biotin tag.

In a second aspect, the present invention provides a method for enrichment of a target DNA comprising the following steps:
 (a) designing a guide sequence for a specific sequence in the target DNA;
 (b) binding the dAgo according to the present invention, the guide sequence and the target DNA to obtain a dAgo-guide sequence-target DNA ternary complex;
 (c) capturing the dAgo-guide sequence-target DNA ternary complex through a capture medium;
 (d) separating the target DNA from the captured dAgo-guide sequence-target DNA ternary complex to obtain an enriched target DNA.

In one embodiment, in order to increase the specificity and binding efficiency of the binding of the dAgo to the guide sequence, the dAgo can be bound to the guide sequence first and then to the target DNA. Therefore, in this embodiment, the above step (b) further comprises the following steps:
 (b1) binding the dAgo according to the present invention with a guide sequence to obtain a dAgo-guide sequence binary complex;
 (b2) binding the dAgo-guide sequence binary complex with the target DNA sequence to obtain a dAgo-guide sequence-target DNA ternary complex.

In one embodiment, the guide sequence is designed for a specific sequence in the target DNA. As used herein, the term "specific sequence" refers to that the sequence is specific with respect to the target DNA. Such specificity enables the guide sequence designed for it to bind to the sequence but not to other nucleotide sequences. The method for designing the guide sequence is known to those skilled in the art. For example, after removing the human genome repeat sequence in the target DNA, a specific sequence is selected at a fixed interval (e.g., every 80 nucleotides), and then the corresponding guide sequence is designed according to the principle of base complementary pairing.

In one embodiment, the guide sequence is an RNA or a DNA. More preferably, the guide sequence is a single stranded RNA (ssRNA) or a single stranded DNA (ssDNA).

In one embodiment, the guide sequence comprises nucleotide modifications, such as 5' phosphorylation, and 5' hydroxylation. Preferably, in order to increase the binding efficiency of the guide sequence to dAgo, the guide sequence comprises 5' phosphorylation modification.

In one embodiment, the guide sequence has a length of 15-25 nucleotides, preferably 18-23 nucleotides, and most preferably 21 nucleotides. The length of the guide sequence affects its binding efficiency with dAgo. Specifically, if a guide sequence is too short, it will affect the specificity of binding. If a guide sequence is too long, it will lead to the formation of an RNA secondary structure (in the case where the guide sequence is an RNA) or lead to difficulty in synthesis.

In one embodiment, the guide sequence is substantially complementary to a specific sequence in the target DNA. In some embodiments, there is a mismatch of no more than 2 bases between the guide sequence and the target DNA.

In one embodiment, that binding of the dAgo, the guide sequence and the target DNA is carry out at a temperature of 85-95° C. In a two-step binding embodiment, the binding of the dAgo to the guide sequence is performed at a temperature of about 93-95° C., and the binding to the target DNA is performed at a temperature of about 85-87° C.

In one embodiment, the dAgo carries a specific tag, including but not limited to a biotin tag and an S-Tag. Preferably, the specific tag is a biotin tag.

In one embodiment, the capture medium includes, but is not limited to, magnetic beads, agarose beads (such as Sepharose™ or Argarose), preferably magnetic beads. Further, the capture medium carries a capture tag capable of binding to a specific tag carried by dAgo, including but not limited to a streptavidin tag and an S-Protein tag. Preferably, the capture medium carries a streptavidin tag.

In the present invention, the capture medium binds to the specific tag carried by dAgo through the capture tag carried by the capture medium, thereby capturing the dAgo-guide sequence-target DNA ternary complex. Capture methods are known in the art, for example, target DNA is captured by incubating biotin-tagged Ago proteins with streptavidin-carrying magnetic beads under appropriate conditions to bind biotin tag with streptavidin. According to the specific experimental needs, those skilled in the art can adjust the specific conditions of capture, such as capture temperature, capture time, and the like.

In one embodiment, methods for separating the target DNA from the captured dAgo-guide sequence-target DNA ternary complexes are also known in the art, for example, magnetic beads capturing the ternary complexes are incubated under appropriate conditions to inactivate streptavidin so as to release the ternary complexes bound thereto, and then the bound protein is removed by protease K to separate the target DNA from the ternary complexes.

In a third aspect, the present invention provides a method for constructing a sequencing library of a target DNA mainly comprising the following steps:
 (1) connecting the target DNA with a sequencing linker to obtain a connection product;
 (2) enriching the target DNA connected with the sequencing linker from the connection product according to the method of the present invention, to obtain an enriched target DNA;
 (3) amplifying the enriched target DNA to obtain the sequencing library.

In another embodiment, the present invention also provides a method for constructing a sequencing library of a target DNA mainly comprising the following steps:
 (1) enriching the target DNA according to the method of the present invention;
 (2) connecting the enriched target DNA with a sequencing linker to obtain a connection product;
 (3) amplifying the connection product to obtain the sequencing library.

In one embodiment, the enriched target DNA can be present on the capture medium, i.e., the target DNA does not need to be separated from the capture medium. In another embodiment, the enriched target DNA is the target DNA separated from the capture medium.

In one embodiment, the method of the present invention can further include a pre-amplification step prior to the enrichment step.

In one embodiment, the sequencing linker is a sequencing linker matching to a sequencing platform. The specific conditions of the connection reaction, such as temperature and reaction time, can be adjusted by those skilled in the art through conventional techniques according to the situation.

In one embodiment, the primer used in the amplification step is a universal primer. As used herein, the term "universal primer" refers to a primer pair that is complementary to the sequence at both ends of the sequencing linker and is capable of amplifying the correctly connected product.

In a fourth aspect, the present invention also provides a kit for carrying out the method according to the present invention, comprising: dAgo, a guide sequence, and a capture medium.

In one embodiment, the guide sequence is an RNA or a DNA. More preferably, the guide sequence is a single stranded RNA (ssRNA) or a single stranded DNA (ssDNA).

In one embodiment, the guide sequence comprises nucleotide modifications, such as 5' phosphorylation, and 5' hydroxylation. Preferably, in order to increase the binding efficiency of the guide sequence to dAgo, the guide sequence comprises 5' phosphorylation modification.

In one embodiment, the guide sequence has a length of 15-25 nucleotides, preferably 18-23 nucleotides, and most preferably 21 nucleotides. The length of the guide sequence affects its binding efficiency with the dAgo. Specifically, if a guide sequence is too short, it will affect the specificity of binding. If a guide sequence is too long, it will lead to the formation of an RNA secondary structure (in the case where the guide sequence is an RNA) or lead to difficulty in synthesis.

In one embodiment, the guide sequence is substantially complementary to the target DNA. In some embodiments, there is a mismatch of no more than 2 bases between the guide sequence and the target DNA.

In one embodiment, the dAgo carries a specific tag, including but not limited to a biotin tags and an S-Tag. Preferably, the specific tag is a biotin tag.

In one embodiment, the capture medium includes, but is not limited to, magnetic beads, agarose beads (such as Sepharose™ or Argarose), preferably magnetic beads. Further, the capture medium carries a capture tag capable of binding to a specific tag carried by dAgo, including but not limited to a streptavidin tag and an S-Protein tag. Preferably, the capture medium carries streptavidin tags.

According to the method and the kit disclosed by the present invention, the enrichment of the target DNA and sequencing based on a second generation high-throughput sequencing platform can be efficiently, rapidly and conveniently realized. In particular, compared with the prior art of the capture method based on the nucleic acid probe and dCas9 capture method, the method and kit of the present invention have the following advantages:

The capture method based on the traditional nucleic acid probe relies on hybridization reaction and requires a reaction time of up to 4 hours or even overnight. The enrichment method of the present invention requires a shorter time, generally 30-60 min.

The enrichment method of the present invention adopts high-temperature washing to increase specificity and simultaneously reduce washing times and avoid loss of the target DNA. Therefore, the binding of the dAgo of the present invention to the guide sequence allows the rapid selection and binding to the target DNA, avoids the problems of long time consumption and complicated operation caused by direct hybridization between the single-stranded nucleic acid probe and the target DNA, and avoids the problem of introducing errors into the target DNA due to long-time hybridization and reduces the loss of the target DNA.

The guide sequence of the present invention is designed for the specific sequence in the target DNA. The sequence is shorter (no more than 25 bases). It is not only easy to synthesize, but also imposes less requirements to the sequence of the target DNA, thereby able to enrich the required target fragments to a greater extent and increases the detection efficiency.

In summary, the method for enriching the target DNA according to the present invention is easy to operate, easy to control quality and cost, and flexible to adjust, and is especially suitable for the enrichment of highly fragmented DNAs (e.g., cfDNAs or severely degraded DNAs from FFPE samples).

BRIEF DESCRIPTION OF THE DRAWINGS

FIG. 2 shows an amino acid sequence SEQ ID NO: 1 of Ago protein (PfAgo) of *Pyrococcus furiosus*, wherein PIWI domain (amino acid residues at positions 473-756) is underlined.

FIG. 3 shows an amino acid sequence SEQ ID NO: 2 of Ago protein (TtAgo) of *Thermus thermophilus*, wherein PIWI domain (amino acid residues at positions 507-671) is underlined.

FIG. 4 shows an amino acid sequence SEQ ID NO: 3 of Ago protein (MjAgo) of *Methanocaldococus jannaschii*, wherein PIWI domain (amino acid residues at positions 426-699) is underlined.

FIG. 5 shows an amino acid sequence SEQ ID NO: 4 of Ago protein (MpAgo) of *Marinitoga piezophila*, wherein PIWI domain (amino acid residues at positions 394-634) is underlined.

FIG. 6 shows an amino acid sequence SEQ ID NO: 5 of Ago protein (TpAgo) of *Thermotoga profunda*, wherein PIWI domain (amino acid residues at positions 431-620) is underlined.

FIG. 7 shows an amino acid sequence SEQ ID NO: 6 of Ago protein (RsAgo) of *Rhodobacter sphaeroides*, wherein PIWI domain (amino acid residues at positions 445-757) is underlined.

FIG. 8 shows an amino acid sequence SEQ ID NO: 7 of Ago protein (AaAgo) of *Aquifex aeolicus*, wherein PIWI domain (amino acid residues at positions 419-694) is underlined.

FIG. 9 shows an amino acid sequence SEQ ID NO: 8 of Ago protein (AfAgo) of *Archaeoblobus fulgidus*, wherein PIWI domain (amino acid residues at positions 110-406) is underlined.

FIG. 10 shows an amino acid sequence alignment of DEDX catalytic regions in PIWI domain of hAGO2 (GenBank Gene ID: 27161), TtAgo, MjAgo, PfAgo, MpAgo, TpAgo, AaAgo, AfAgo and RsAgo. Among them, the DEDX catalytic regions shown are amino acid residues at positions 553-563/591-600/623-631/740-750 of SEQ ID NO: 1, amino acid residues at positions 473-483/511-519/541-549/655-665 of SEQ ID NO: 2, amino acid residues at positions 499-509/540-548/565-573/683-693 of SEQ ID NO: 3, amino acid residues at positions 441-451/481-489/ 511-521/619-629 of SEQ ID NO: 4, amino acid residues at positions 434-444/474-482/504-514/612-622 of SEQ ID NO: 5, amino acid residues at positions 524-534/695-703/ 549-559/461-471 of SEQ ID NO: 6, amino acid residues at positions 463-471/497-507/566-576/678-688 of SEQ ID NO: 7, and amino acid residues at positions 169-179/136-144/200-210/121-131 of SEQ ID NO: 8. FIG. 10 discloses SEQ ID NOS: 17-20 and 31-62, respectively, in order of appearance.

FIG. 11 discloses SEQ ID NOS: 21-24, 23, and 25-29, respectively, in order of columns.

DETAILED DESCRIPTION OF THE INVENTION

The present invention is described below in detail with reference to the drawings and the examples. It should be noted that those skilled in the art should understand that the drawings and the examples of the present invention are for the purpose of illustration only and do not constitute any limitation to the present invention.

Example 1: Preparation of Ago Protein Mutant of the Present Invention

Step 1: Constructing an Expression Vector

A biotin receptor sequence was connected to the N-terminal of the amino acid sequence (SEQ ID NO: 1) of the known *Pyrococcus fuliginosus* Ago protein (PfAgo), and a codon optimized nucleotide sequence for *Escherichia coli* (*E. coli*) was designed and synthesized according to the biotin receptor sequence. The nucleotide sequence, 6× His-Tag (SEQ ID NO: 30), PfAgo-BAS, IRES, and BirA (*E. coli* biotin ligase) were serially cloned into pET-28a vector with a kanamycin resistance gene in sequence to obtain a vector pPFA-1.0.

The pPFA-1.0 was subjected to site-directed mutation according to the operation protocol of the manual using Q5® Site-Directed Mutagenesis Kit (NEB, Cat #E05454S). The mutated DNA was transformed into *E. Coli* DH5α☐cells and cultured overnight at 37° C. in LB agarose medium containing kanamycin. For each mutation, 10 colonies were selected and cultured in 4 mL LB liquid medium containing kanamycin under shaking at 37° C. for 12-16 hours. Then, 2 mL of bacterial liquid was taken to extract plasmids using Plasmid Mini Kit (Qiagen®, Cat #27104).

Step 2: Sequencing Verification

Figure 1:
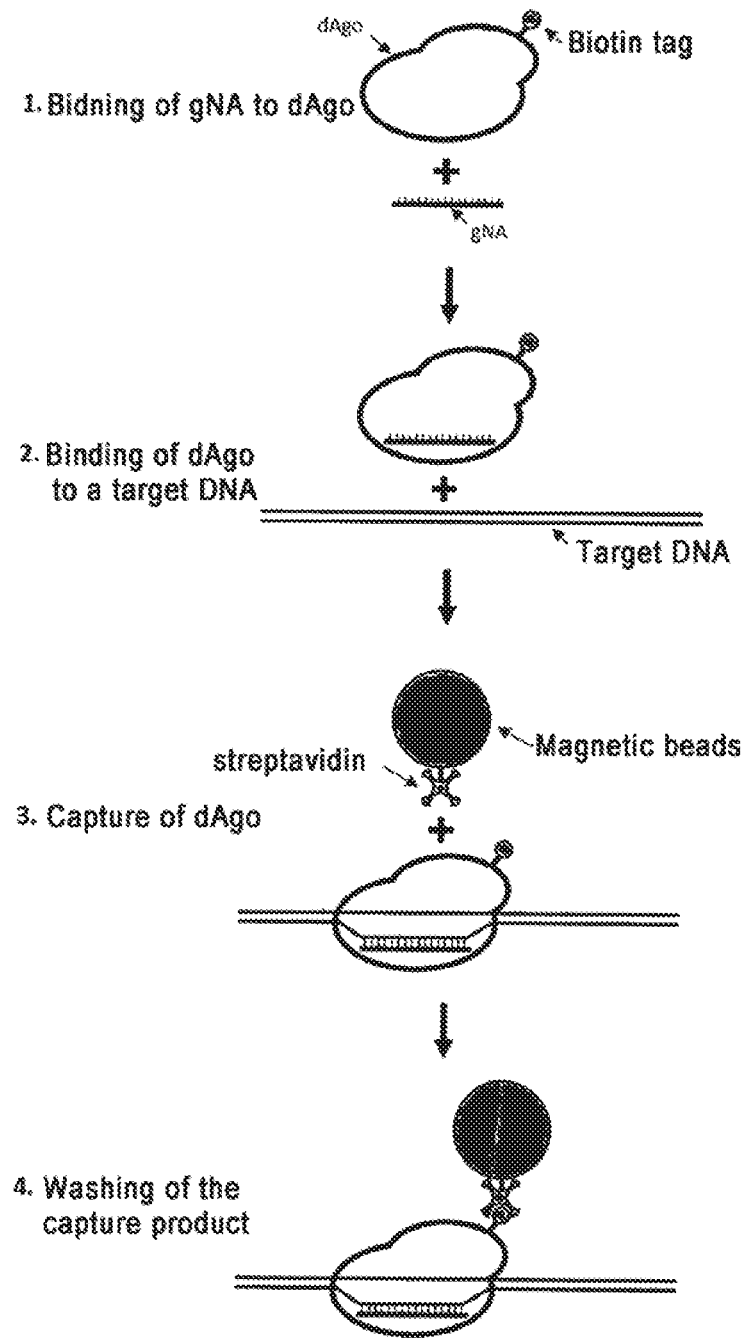
FIG. 1 is a flow chart illustrating a method of the enrichment of the target DNA according to the present invention.
Figure 11:
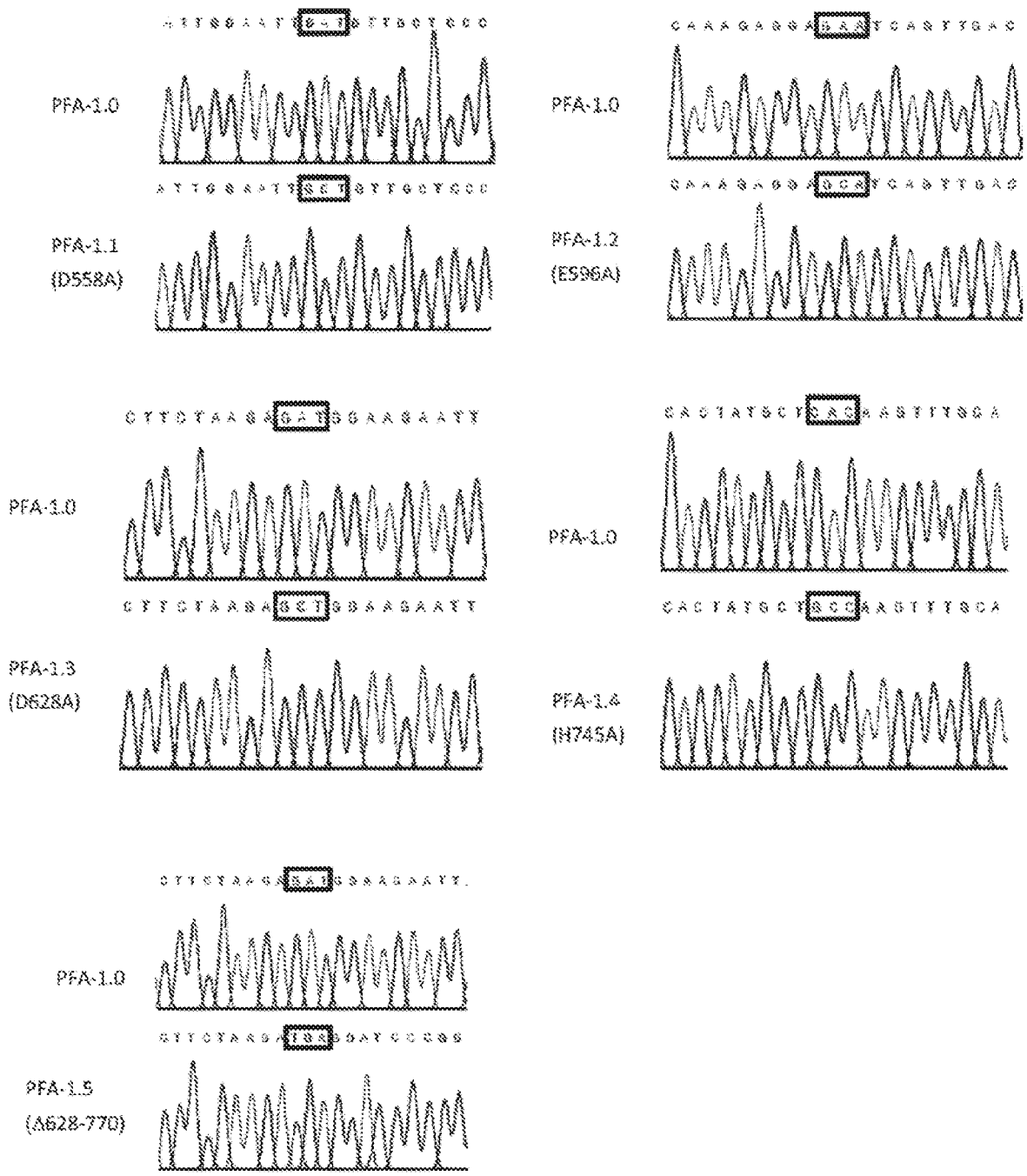
FIG. 11 shows the sequencing results of pPFA-1.1, pPFA-1.2, pPFA-1.3, pPFA-1.4, and pPFA-1.5.

The extracted plasmid was amplified using universal primers on the plasmid (T7 promoter primer 5'-TAATACGACTCACTATAGGG-3' (SEQ ID NO: 13) and T7 terminator primer 5'-GCTAGTTATTGCTCAGCGG-3' (SEQ ID NO: 14), synthesized by IDT), and then the amplified products were sequenced (Beijing Ruibo Xingke Biotechnology Co., Ltd.). The sequencing results are shown in FIG. 11.

The following plasmids confirmed to contain mutations were stored at −20° C. for a long time:

plasmid pPFA-1.1, wherein the amino acid residue at position 558 is substituted by alanine (D558A);

plasmid pPFA-1.2, wherein the amino acid residue at position 596 is substituted by alanine (E596A);

plasmid pPFA-1.3, wherein the amino acid residue at position 628 is substituted by alanine (D628A);

plasmid pPFA-1.4, wherein the amino acid residue at position 745 is substituted by alanine (H745A); and plasmid pPFA-1.5, wherein the amino acid residues at positions 628-770 are deleted (Δ628-770).

Step 3: Vector Transformation and Expression of PfAgo Protein Mutant

The five plasmids confirmed to be mutated in above step 2 were transformed into *E. coli* BL21 (DE3) cells, respectively. The transformed cells were cultured at 37° C. under shaking overnight in LB culture medium containing 50 μg/mL kanamycin. Then, the medium was replaced with fresh LB culture medium, and the culture was continued to expand until $OD_{600}$ reached 0.4-0.8. IPTG was added until the final concentration is 500 μM, and the culture continued at 37° C. under shaking for 3-5 hours.

The culture medium was centrifuged at 6,000 g for 15 minutes to remove the supernatant. The resulting pellet was resuspended in cell lysis buffer I (20 mM Tris pH 8.0, 1 M NaCl, 2 mM $MnCl_2$) and ultrasonically disrupted. The disrupted solution was centrifuged at 20,000 g for 30 minutes at 4° C., and then the supernatant was collected. The supernatant was purified with nickel column at 4° C., and then the purified product was desalted and concentrated using a protein ultrafiltration column (Pierce™ Protein Concentrator PES, 30K MWCO, Thermo Fisher Scientific) according to the operation protocol of the manual. The concentrated product is the expressed PfAgo protein mutant carrying a biotin tag. The expressed PfAgo protein mutant was added with equal volume of glycerol and stored at −20° C.

Example 2: Enrichment of Target DNA According to the Method of the Present Invention The target DNA in this example is exons 18-21 fragment of EGFR gene from free DNAs in plasma sample and genomic DNAs in leukocytes isolated from normal human peripheral blood, respectively.

Step 1: DNA Extraction

For free DNAs: 4 mL of human plasma was taken, and the free DNAs were extracted using QIAamp Circulating Nucleic Acid Kit (Qiagen®, Cat #55114) according to the kit manual, and then eluted with 45 μL Elution Buffer.

For genomic DNAs: 200 μL of leukocytes isolated from human peripheral blood were taken, and the genomic DNA was extracted using MagJET™ Whole Blood gDNA Kit (Thermo Scientific™, Cat #K2741) according to the kit manual. Approximately 500 ng (30 μL) of extracted genomic DNA was ultrasonically disrupted (ultrasonic disruptor Bioruptor® Pico from Diagenode SA).

Step 2: Design of Guide DNA (gDNA)

The gDNA with 5' phosphorylation modification was designed and synthesized according to EGFR exons 18, 19, 20 and 21 sequences as follows:

| gDNA Name | gDNA sequences (5'-3') |
|---|---|
| EGFR_E18_gD1 | CTCCCAACCAAGCTCTCTTG (SEQ ID NO: 9) |
| EGFR_E19_gD1 | TAGGGACTCTGGATCCCAGA (SEQ ID NO: 10) |
| EGFR_E20_gD2 | TGAGGCAGATGCCCAGCAGG (SEQ ID NO: 11) |
| EGFR_E21_gD1 | TCTGTGATCTTGACATGCTG (SEQ ID NO: 12) |

100 µM of the above-mentioned gDNAs were dissolved in Buffer EB (20 mM Tris pH 8.0), respectively. Then, each of the gDNA solutions were mixed in equal volume and diluted 100 times to obtain 1 µM gDNA mixed solution.

Step 3: Binding of gDNA to PfAgo Protein Mutant to Form a Binary Complex.

The reaction system was prepared by mixing each PfAgo protein mutant (i.e., D558A, E596A, D628A, H745A and Δ628-770) and gDNA according to the following table:

| Reagent Name | Volume |
| --- | --- |
| Buffer DA1 (2x) | 10 uL |
| PfAgo protein mutant (5 uM) | 0.5 uL |
| gDNA mixed solution (1 uM) | 5 uL |
| ddH$_2$O | 4.5 uL |

The above reaction system was incubated at 95° C. for 10 minutes.

Step 4: Binding of the Binary Complex to the Target DNA to Form a Ternary Complex.

45 µL of free DNA or 30 µL of ultrasonically disrupted genomic DNA obtained in the above step 1 was added to the reaction system in the above step 3, mixed evenly, incubated at 87° C. for 15 minutes, and then placed on ice.

Step 5: Capture of the Ternary Complex.

Dynabeads™ M270 Streptavidin (Thermo Fisher, Cat #65305) pre-balanced with Buffer DA1(1x) were added to the reaction system in the above step 4 and incubated at room temperature for 30 minutes. Then Dynabeads™ were washed with Buffer DA1(1x) 3 times at room temperature for 3 minutes each time. At this time, Dynabeads™ were bound with the enriched target DNA.

Step 6: Separation of Enriched Target DNA

50 µL Buffer DA1(1x) and 1 µL protease K (20 µg/µL) were added to Dynabeads™ and incubated at 55° C. for 15 minutes. Then, it was placed on ice, cooled and added with double volume of Agencourt AMPure XP magnetic beads (Beckman Coulter™, Cat #A63880). After incubation for 10 minutes at room temperature, the magnetic beads were adsorbed to remove supernatant, washed twice with 80% alcohol, and finally dissolved in 25 µL Tris solution (20 mM, pH 8.5).

Step 7: Quality Analysis of Enriched Target DNA

Figures 12, 13:
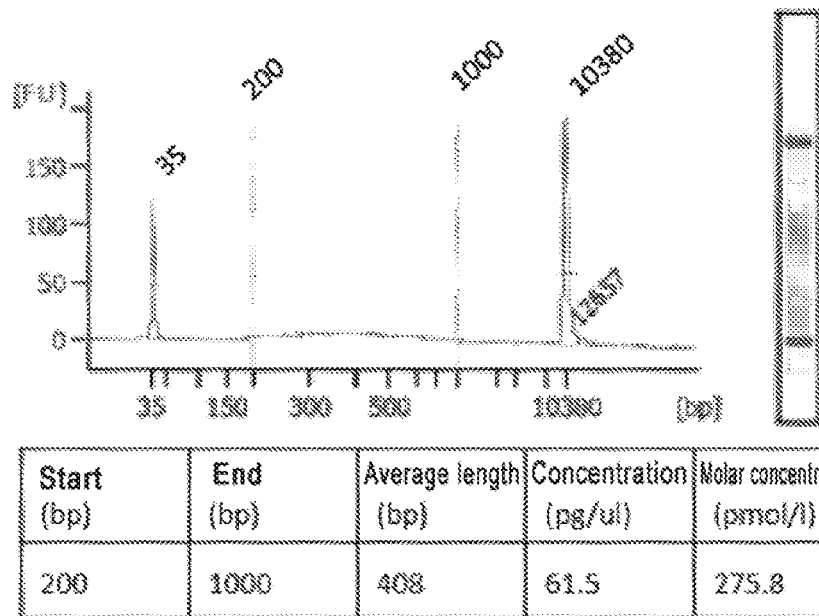
FIG. 12 shows the quality analysis results of the target DNA enriched according to the method of Example 2.
FIG. 13 shows the representative sequencing results of the sequencing library prepared according to the methods of Example 3 and Example 4.

Purified DNA was tested for DNA concentration on Qubit® 3 Fluorometer (Thermo Fisher, Cat #Q33216) with Qubit® dsDNA Hs reagent (Thermo Fisher, Cat #Q3323), and DNA purity was tested by capillary electrophoresis simultaneously (Agilent 2100 Bio Analyzer Instrument, Cat #G2939BA). The representative results are shown in FIG. 12. The enriched target DNA has a length of around 200-1000 bp. The concentration is 61.5 pg/µL. The molar concentration reaches 275.8 pmol/l. The quality is good and complies with the requirements of preparing library for sequencing.

Example 3: Construction of Sequencing Library of Target DNA According to the Method of the Present Invention Step 1: Extraction of Free DNA 4 mL of human plasma was taken, and free DNA was extracted using QIAamp Circulating Nucleic Acid Kit (Qiagen®, Cat #55114) according to the kit manual. The final free DNA was eluted with 45 µL Elution Buffer provided by the kit.

Step 2: Connection of Sequencing Linker

The free DNA was subjected to terminal filling and A addition, and then connected to TruSeq linker suitable for Illumina® sequencing platform using KAPA HyperPrep Kit (Kapa Biosystems, Cat #KKK8501) according to the manual protocol.

Step 3: Pre-Amplification of the Connection Product

The reaction system was prepared according to the following table:

| | |
| --- | --- |
| NEBNext® Ultra™ II Q5® Mater Mix 2x (NEB, Cat#M0544S) | 50 uL |
| P5/P7 Universal Primer Mixture (each 20 uM) (synthesized by IDT, P5: 5'-AATGATACGGCGACCACCGA-3' (SEQ ID NO: 15) P7: 5'-CAAGCAGAAGACGGCATACGAGAT-3' (SEQ ID NO: 16)) | 5 uL |
| Connection product | 45 uL |

Pre-amplification was carried out on a PCR instrument according to the following conditions:

| Temperature | Time | Number of cycle |
| --- | --- | --- |
| 98° C. | 60 sec | 1 |
| 98° C. | 15 sec | 15 |
| 60° C. | 30 sec | |
| 65° C. | 30 sec | |
| 65° C. | 3 min | 1 |

After amplification was completed, the pre-amplification product was purified according to the manufacturer's manual with 200 µL of Agencourt AMPure XP magnetic beads (Beckman Coulter™, Cat #A63880). The purified product was dissolved in 30 µL buffer DA1 (1x) (15 mm Tris pH 8.0, 0.5 mm MnCl$_2$, 250 mm NaCl).

Step 4: Enrichment of Target DNA

Guide DNA (gDNA) with 5' phosphorylation modification was designed and synthesized according to exons 18, 19, 20 and 21 sequences of EGFR gene as follows:

| gDNA Name | gDNA sequences (5'-3') |
| --- | --- |
| EGFR_E18_gD1 | CTCCCAACCAAGCTCTCTTG (SEQ ID NO: 9) |
| EGFR_E19_gD1 | TAGGGACTCTGGATCCCAGA (SEQ ID NO: 10) |
| EGFR_E20_gD2 | TGAGGCAGATGCCCAGCAGG (SEQ ID NO: 11) |
| EGFR_E21_gD1 | TCTGTGATCTTGACATGCTG (SEQ ID NO: 12) |

100 µM of the above-mentioned gDNAs were dissolved in Buffer EB (20 mM Tris pH 8.0), respectively. Then, each of the gDNA solutions were mixed in equal volume and diluted 100 times to obtain 1 µM gDNA mixed solution.

The reaction system was prepared by mixing PfAgo protein mutant (i.e., D558A, E596A, D628A, H745A and Δ628-770) and gDNA according to the following table:

| Reagent Name | Volume |
| --- | --- |
| Buffer DA1 (2x)* | 10 uL |
| PfAgo protein mutant (5 uM) | 0.5 uL |

-continued

| Reagent Name | Volume |
|---|---|
| gDNA mixed solution (1 uM) | 5 uL |
| ddH$_2$O | 4.5 uL |

*Buffer DA1(2x): 30 mM Tris pH 8.0, 1.0 mM MnCl$_2$, 500 mM NaCl

The above reaction system was incubated at 95° C. for 10 minutes.

30 μL of the purified product obtained in step 3 was added to the above reaction system, mixed evenly, incubated at 87° C. for 15 minutes, and then placed on ice.

Dynabeads™ M270 Streptavidin (Thermo Fisher, Cat #65305) pre-balanced with Buffer DA1(1x) were added to the above reaction system and incubated at room temperature for 30 minutes. Then, Dynabeads™ were washed with Buffer DA1(1x) 3 times at room temperature for 3 minutes each time. At this time, Dynabeads™ were bound with enriched target DNA.

Step 5: Amplification of the Enriched Target DNA

The following reagents were added to Dynabeads™ obtained in step 4.

| Reagent Name | Volume |
|---|---|
| NEBNext ® Ultra ™ II Q5 ® Mater Mix 2x | 25 uL |
| P5/P7 Universal Primer Mixture (each 20 uM) | 2.5 uL |
| deionized water | 22.5 uL |

Amplification was performed on a PCR instrument under the following conditions:

| Temperature | Time | Number of cycle |
|---|---|---|
| 98° C. | 60 sec | 1 |
| 98° C. | 15 sec | 15 |
| 60° C. | 30 sec | |
| 65° C. | 30 sec | |
| 65° C. | 3 min | 1 |

Step 6: Purification of the Amplified Target DNA

To the amplification product obtained in step 5 above, equal volume of Agencourt AMPure XP magnetic beads (Beckman Coulter™, Cat #A63880) were added, incubated at room temperature for 5 minutes, and then washed twice with 200 μl of 80% ethanol. After air drying at room temperature, 30 μl Buffer EB was added and the supernatant was collected after standing for 5 min. The supernatant is the enriched and purified target DNA sequencing library.

Example 4: Construction of Sequencing Library of Target DNA According to the Method of the Present Invention The enriched target DNA obtained in step 6 of Example 2 was subjected to terminal filling and A addition using KAPA Hyper Prep kit (Kapa Biosystems, Cat #KK8501) and according to the kit manual (the enriched target DNA combined with Dynabeads™ obtained in step 5 of Example 2 can also be used), and then connected with TruSeq linker suitable for Illumina® sequencing platform to obtain a connection product.

The following reagents were added to the above-mentioned connection product:

| Reagent Name | Volume |
|---|---|
| NEBNext ® Ultra ™ II Q5 ® Mater Mix 2x | 25 uL |
| P5/P7 Universal Primer Mixture (each 20 uM) | 2.5 uL |
| deionized water | 22.5 uL |

Amplification was performed on a PCR instrument under the following conditions:

| Temperature | Time | Number of cycle |
|---|---|---|
| 98° C. | 60 sec | 1 |
| 98° C. | 15 sec | 15 |
| 60° C. | 30 sec | |
| 65° C. | 30 sec | |
| 65° C. | 3 min | 1 |

After completion of amplification, equal volume of Agencourt AMPure XP magnetic beads (Beckman Coulter, Cat #A63880) were added to the amplification product, incubated at room temperature for 5 minutes, and then washed twice with 200 μl of 80% ethanol. After air drying at room temperature, 30 μl buffer EB was added and the supernatant was collected after standing for 5 minutes. The supernatant is the enriched and purified target DNA sequencing library.

Example 5: Computer Sequencing

The sequencing libraries obtained in Examples 3 and 4 were quantified on a StepOnePlus™ Real-Time PCR System (ThermoFisher, Cat #4376592) fluorescence quantitative PCR instrument using KAPA Library Quantification Kits (KAPA Biosciences, Cat #KK4835) and according to the kit manual. The effective concentration for quantitative detection of the sequencing library was not less than 1 nM.

According to the concentration of the library, the sequencing library with an appropriate volume was sequenced by double-ended 150 bases (150PE) on Illumina® NextSeq CN500 sequencer. The representative sequencing results are shown in FIG. 13. The target DNA fragment in the genomic DNA and free DNA were enriched for around 500 times by the Ago protein mutant of the present invention. Thus, for the genomic DNA and highly fragmented free DNA, the present invention could rapidly and efficiently enrich the target DNA using Ago protein mutant, thereby constructing the sequencing library meeting the sequencing requirements.

It should be noted that although some features of the present invention have been illustrated by the above examples, they cannot be used to limit the present invention. Various modifications and changes can be made to the present invention for those skilled in the Art. Reaction reagents, reaction conditions and the like involved in the construction of sequencing library can be adjusted and changed according to specific needs. Therefore, for those skilled in the art, several simple substitutions can be made without departing from the concepts and principles of the present invention, which should be included in the protection scope of the present invention.

The invention claimed is:

1. A mutant of Argonaute protein, having a DNA binding activity but lacking a DNA cleavage activity, wherein the mutation of the mutant is located in a PIWI domain, wherein the amino acid sequence of the Argonaute protein is as shown in SEQ ID NO: 1, and wherein amino acids at positions 628-770 of SEQ ID NO: 1 are deleted.

2. The mutant of claim 1, wherein the mutant further comprises mutations located in the following domains: N-terminal domain and PAZ domain.

3. A method for enrichment of a target DNA comprising the following steps:
   (a) designing a guide sequence for a specific sequence in the target DNA;
   (b) binding the mutant of claim 1, the guide sequence and the target DNA to obtain a mutant-guide sequence-target DNA ternary complex;
   (c) capturing the mutant-guide sequence-target DNA ternary complex through a capture medium;
   (d) separating the target DNA from the captured mutant-guide sequence-target DNA ternary complex to obtain an enriched target DNA.

4. The method of claim 3, wherein the step (b) further comprises the following steps:
   (b1) binding the mutant of claim 1 with a guide sequence to obtain a mutant-guide sequence binary complex;
   (b2) binding the mutant-guide sequence binary complex with the target DNA sequence to obtain a mutant-guide sequence-target DNA ternary complex.

5. The method of claim 3, wherein the guide sequence is a DNA.

6. The method of claim 3, wherein the guide sequence is a single stranded DNA (ssDNA).

7. The method of claim 3, wherein the guide sequence comprises nucleotide modifications.

8. The method of claim 7, wherein the modification is 5' phosphorylation or 5' hydroxylation.

9. The method of claim 3, wherein the guide sequence has a length of 15-25 nucleotides.

10. The method of claim 3, wherein the guide sequence is substantially complementary to the specific sequence in the target DNA.

11. The method of claim 3, wherein the capture medium is magnetic beads.

12. The method of claim 3, wherein the capture medium carries a capture tag capable of binding to the specific tag carried by the mutant.

13. A kit comprising the mutant of claim 1.

14. The kit of claim 13, further comprising a guide sequence and a capture medium.

15. The kit of claim 14, wherein the guide sequence is a DNA.

* * * * *

SEQUENCE LISTING

<160> NUMBER OF SEQ ID NOS: 62

<210> SEQ ID NO 1
<211> LENGTH: 770
<212> TYPE: PRT
<213> ORGANISM: Pyrococcus furiosus

<400> SEQUENCE: 1

```
Met Lys Ala Lys Val Val Ile Asn Leu Val Lys Ile Asn Lys Lys Ile
1               5                   10                  15

Ile Pro Asp Lys Ile Tyr Val Tyr Arg Leu Phe Asn Asp Pro Glu Glu
                20                  25                  30

Glu Leu Gln Lys Glu Gly Tyr Ser Ile Tyr Arg Leu Ala Tyr Glu Asn
            35                  40                  45

Val Gly Ile Val Ile Asp Pro Glu Asn Leu Ile Ile Ala Thr Thr Lys
50                  55                  60

Glu Leu Glu Tyr Glu Gly Glu Phe Ile Pro Glu Gly Glu Ile Ser Phe
65                  70                  75                  80

Ser Glu Leu Arg Asn Asp Tyr Gln Ser Lys Leu Val Leu Arg Leu Leu
                85                  90                  95

Lys Glu Asn Gly Ile Gly Glu Tyr Glu Leu Ser Lys Leu Leu Arg Lys
            100                 105                 110

Phe Arg Lys Pro Lys Thr Phe Gly Asp Tyr Lys Val Ile Pro Ser Val
        115                 120                 125

Glu Met Ser Val Ile Lys His Asp Glu Asp Phe Tyr Leu Val Ile His
130                 135                 140

Ile Ile His Gln Ile Gln Ser Met Lys Thr Leu Trp Glu Leu Val Asn
145                 150                 155                 160

Lys Asp Pro Lys Glu Leu Glu Glu Phe Leu Met Thr His Lys Glu Asn
                165                 170                 175

Leu Met Leu Lys Asp Ile Ala Ser Pro Leu Lys Thr Val Tyr Lys Pro
            180                 185                 190

Cys Phe Glu Glu Tyr Thr Lys Lys Pro Lys Leu Asp His Asn Gln Glu
        195                 200                 205

Ile Val Lys Tyr Trp Tyr Asn Tyr His Ile Glu Arg Tyr Trp Asn Thr
210                 215                 220

Pro Glu Ala Lys Leu Glu Phe Tyr Arg Lys Phe Gly Gln Val Asp Leu
225                 230                 235                 240

Lys Gln Pro Ala Ile Leu Ala Lys Phe Ala Ser Lys Ile Lys Lys Asn
                245                 250                 255

Lys Asn Tyr Lys Ile Tyr Leu Leu Pro Gln Leu Val Val Pro Thr Tyr
            260                 265                 270

Asn Ala Glu Gln Leu Glu Ser Asp Val Ala Lys Glu Ile Leu Glu Tyr
        275                 280                 285

Thr Lys Leu Met Pro Glu Glu Arg Lys Glu Leu Leu Glu Asn Ile Leu
            290                 295                 300

Ala Glu Val Asp Ser Asp Ile Ile Asp Lys Ser Leu Ser Glu Ile Glu
305                 310                 315                 320

Val Glu Lys Ile Ala Gln Glu Leu Glu Asn Lys Ile Arg Val Arg Asp
                325                 330                 335

Asp Lys Gly Asn Ser Val Pro Ile Ser Gln Leu Asn Val Gln Lys Ser
            340                 345                 350

Gln Leu Leu Leu Trp Thr Asn Tyr Ser Arg Lys Tyr Pro Val Ile Leu
        355                 360                 365
```

```
Pro Tyr Glu Val Pro Glu Lys Phe Arg Lys Ile Arg Glu Ile Pro Met
    370             375                 380

Phe Ile Ile Leu Asp Ser Gly Leu Leu Ala Asp Ile Gln Asn Phe Ala
385                 390                 395                 400

Thr Asn Glu Phe Arg Glu Leu Val Lys Ser Met Tyr Tyr Ser Leu Ala
            405                 410                 415

Lys Lys Tyr Asn Ser Leu Ala Lys Lys Ala Arg Ser Thr Asn Glu Ile
            420                 425                 430

Gly Leu Pro Phe Leu Asp Phe Arg Gly Lys Lys Val Ile Thr Glu
        435                 440                 445

Asp Leu Asn Ser Asp Lys Gly Ile Ile Glu Val Val Glu Gln Val Ser
    450                 455                 460

Ser Phe Met Lys Gly Lys Glu Leu Gly Leu Ala Phe Ile Ala Ala Arg
465                 470                 475                 480

Asn Lys Leu Ser Ser Glu Lys Phe Glu Glu Ile Lys Arg Arg Leu Phe
                485                 490                 495

Asn Leu Asn Val Ile Ser Gln Val Val Asn Glu Asp Thr Leu Lys Asn
            500                 505                 510

Lys Arg Asp Lys Tyr Asp Arg Asn Arg Leu Asp Leu Phe Val Arg His
        515                 520                 525

Asn Leu Leu Phe Gln Val Leu Ser Lys Leu Gly Val Lys Tyr Tyr Val
    530                 535                 540

Leu Asp Tyr Arg Phe Asn Tyr Asp Tyr Ile Ile Gly Ile Asp Val Ala
545                 550                 555                 560

Pro Met Lys Arg Ser Glu Gly Tyr Ile Gly Gly Ser Ala Val Met Phe
            565                 570                 575

Asp Ser Gln Gly Tyr Ile Arg Lys Ile Val Pro Ile Lys Ile Gly Glu
        580                 585                 590

Gln Arg Gly Glu Ser Val Asp Met Asn Glu Phe Phe Lys Glu Met Val
    595                 600                 605

Asp Lys Phe Lys Glu Phe Asn Ile Lys Leu Asp Asn Lys Lys Ile Leu
    610                 615                 620

Leu Leu Arg Asp Gly Arg Ile Thr Asn Asn Glu Glu Glu Gly Leu Lys
625                 630                 635                 640

Tyr Ile Ser Glu Met Phe Asp Ile Glu Val Val Thr Met Asp Val Ile
            645                 650                 655

Lys Asn His Pro Val Arg Ala Phe Ala Asn Met Lys Met Tyr Phe Asn
        660                 665                 670

Leu Gly Gly Ala Ile Tyr Leu Ile Pro His Lys Leu Lys Gln Ala Lys
        675                 680                 685

Gly Thr Pro Ile Pro Ile Lys Leu Ala Lys Arg Ile Ile Lys Asn
    690                 695                 700

Gly Lys Val Glu Lys Gln Ser Ile Thr Arg Gln Asp Val Leu Asp Ile
705                 710                 715                 720

Phe Ile Leu Thr Arg Leu Asn Tyr Gly Ser Ile Ser Ala Asp Met Arg
                725                 730                 735

Leu Pro Ala Pro Val His Tyr Ala His Lys Phe Ala Asn Ala Ile Arg
            740                 745                 750

Asn Glu Trp Lys Ile Lys Glu Glu Phe Leu Ala Glu Gly Phe Leu Tyr
        755                 760                 765

Phe Val
    770
```

```
<210> SEQ ID NO 2
<211> LENGTH: 685
<212> TYPE: PRT
<213> ORGANISM: Thermus thermophilus

<400> SEQUENCE: 2
```

| | | | | | | | | | | | | | | |
|---|---|---|---|---|---|---|---|---|---|---|---|---|---|---|
| Met | Asn | His | Leu | Gly | Lys | Thr | Glu | Val | Phe | Leu | Asn | Arg | Phe | Ala | Leu |
| 1 | | | | 5 | | | | | 10 | | | | | 15 | |

| Arg | Pro | Leu | Asn | Pro | Glu | Glu | Leu | Arg | Pro | Trp | Arg | Leu | Glu | Val | Val |
| | | | 20 | | | | | 25 | | | | | 30 | | |

| Leu | Asp | Pro | Pro | Gly | Arg | Glu | Val | Tyr | Pro | Leu | Leu | Ala | Gln |
| | | 35 | | | | | 40 | | | | | 45 | |

| Val | Ala | Arg | Arg | Ala | Gly | Gly | Val | Thr | Val | Arg | Met | Gly | Asp | Gly | Leu |
| | 50 | | | | | 55 | | | | | 60 | | | | |

| Ala | Ser | Trp | Ser | Pro | Pro | Glu | Val | Leu | Val | Leu | Glu | Gly | Thr | Leu | Ala |
| 65 | | | | | 70 | | | | | 75 | | | | | 80 |

| Arg | Met | Gly | Gln | Thr | Tyr | Ala | Tyr | Arg | Leu | Tyr | Pro | Lys | Gly | Arg | Arg |
| | | | | 85 | | | | | 90 | | | | | 95 | |

| Pro | Leu | Asp | Pro | Lys | Asp | Pro | Gly | Glu | Arg | Ser | Val | Leu | Ser | Ala | Leu |
| | | | 100 | | | | | 105 | | | | | 110 | | |

| Ala | Arg | Arg | Leu | Leu | Gln | Glu | Arg | Leu | Arg | Arg | Leu | Glu | Gly | Val | Trp |
| | | 115 | | | | | 120 | | | | | 125 | | | |

| Val | Glu | Gly | Leu | Ala | Val | Tyr | Arg | Arg | Glu | His | Ala | Arg | Gly | Pro | Gly |
| | 130 | | | | | 135 | | | | | 140 | | | | |

| Trp | Arg | Val | Leu | Gly | Gly | Ala | Val | Leu | Asp | Leu | Trp | Val | Ser | Asp | Ser |
| 145 | | | | | 150 | | | | | 155 | | | | | 160 |

| Gly | Ala | Phe | Leu | Leu | Glu | Val | Asp | Pro | Ala | Tyr | Arg | Ile | Leu | Cys | Glu |
| | | | | 165 | | | | | 170 | | | | | 175 | |

| Met | Ser | Leu | Glu | Ala | Trp | Leu | Ala | Gln | Gly | His | Pro | Leu | Pro | Lys | Arg |
| | | | 180 | | | | | 185 | | | | | 190 | | |

| Val | Arg | Asn | Ala | Tyr | Asp | Arg | Arg | Thr | Trp | Glu | Leu | Leu | Arg | Leu | Gly |
| | | 195 | | | | | 200 | | | | | 205 | | | |

| Glu | Glu | Asp | Pro | Lys | Glu | Leu | Pro | Leu | Pro | Gly | Gly | Leu | Ser | Leu | Leu |
| | 210 | | | | | 215 | | | | | 220 | | | | |

| Asp | Tyr | His | Ala | Ser | Lys | Gly | Arg | Leu | Gln | Gly | Arg | Glu | Gly | Gly | Arg |
| 225 | | | | | 230 | | | | | 235 | | | | | 240 |

| Val | Ala | Trp | Val | Ala | Asp | Pro | Lys | Asp | Pro | Arg | Lys | Pro | Ile | Pro | His |
| | | | | 245 | | | | | 250 | | | | | 255 | |

| Leu | Thr | Gly | Leu | Leu | Val | Pro | Val | Leu | Thr | Leu | Glu | Asp | Leu | His | Glu |
| | | | 260 | | | | | 265 | | | | | 270 | | |

| Glu | Glu | Gly | Ser | Leu | Ala | Leu | Ser | Leu | Pro | Trp | Glu | Arg | Arg | Arg |
| | | 275 | | | | | 280 | | | | | 285 | | |

| Arg | Thr | Arg | Glu | Ile | Ala | Ser | Trp | Ile | Gly | Arg | Arg | Leu | Gly | Leu | Gly |
| | 290 | | | | | 295 | | | | | 300 | | | | |

| Thr | Pro | Glu | Ala | Val | Arg | Ala | Gln | Ala | Tyr | Arg | Leu | Ser | Ile | Pro | Lys |
| 305 | | | | | 310 | | | | | 315 | | | | | 320 |

| Leu | Met | Gly | Arg | Arg | Ala | Val | Ser | Lys | Pro | Ala | Asp | Ala | Leu | Arg | Val |
| | | | | 325 | | | | | 330 | | | | | 335 | |

| Gly | Phe | Tyr | Arg | Ala | Gln | Glu | Thr | Ala | Leu | Ala | Leu | Leu | Arg | Leu | Asp |
| | | | 340 | | | | | 345 | | | | | 350 | | |

| Gly | Ala | Gln | Gly | Trp | Pro | Glu | Phe | Leu | Arg | Arg | Ala | Leu | Leu | Arg | Ala |
| | | 355 | | | | | 360 | | | | | 365 | | | |

| Phe | Gly | Ala | Ser | Gly | Ala | Ser | Leu | Arg | Leu | His | Thr | Leu | His | Ala | His |
| | 370 | | | | | 375 | | | | | 380 | | | | |

-continued

```
Pro Ser Gln Gly Leu Ala Phe Arg Glu Ala Leu Arg Lys Ala Lys Glu
385                 390                 395                 400

Glu Gly Val Gln Ala Val Leu Val Leu Thr Pro Pro Met Ala Trp Glu
            405                 410                 415

Asp Arg Asn Arg Leu Lys Ala Leu Leu Leu Arg Glu Gly Leu Pro Ser
        420                 425                 430

Gln Ile Leu Asn Val Pro Leu Arg Glu Glu Arg His Arg Trp Glu
    435                 440                 445

Asn Ala Leu Leu Gly Leu Leu Ala Lys Ala Gly Leu Gln Val Val Ala
450                 455                 460

Leu Ser Gly Ala Tyr Pro Ala Glu Leu Ala Val Gly Phe Asp Ala Gly
465                 470                 475                 480

Gly Arg Glu Ser Phe Arg Phe Gly Ala Ala Cys Ala Val Gly Gly
            485                 490                 495

Asp Gly Gly His Leu Leu Trp Thr Leu Pro Glu Ala Gln Ala Gly Glu
        500                 505                 510

Arg Ile Pro Gln Glu Val Val Trp Asp Leu Leu Glu Glu Thr Leu Trp
    515                 520                 525

Ala Phe Arg Arg Lys Ala Gly Arg Leu Pro Ser Arg Val Leu Leu Leu
            530                 535                 540

Arg Asp Gly Arg Val Pro Gln Asp Glu Phe Ala Leu Ala Leu Glu Ala
545                 550                 555                 560

Leu Ala Arg Glu Gly Ile Ala Tyr Asp Leu Val Ser Val Arg Lys Ser
            565                 570                 575

Gly Gly Gly Arg Val Tyr Pro Val Gln Gly Arg Leu Ala Asp Gly Leu
            580                 585                 590

Tyr Val Pro Leu Glu Asp Lys Thr Phe Leu Leu Leu Thr Val His Arg
            595                 600                 605

Asp Phe Arg Gly Thr Pro Arg Pro Leu Lys Leu Val His Glu Ala Gly
        610                 615                 620

Asp Thr Pro Leu Glu Ala Leu Ala His Gln Ile Phe His Leu Thr Arg
625                 630                 635                 640

Leu Tyr Pro Ala Ser Gly Phe Ala Phe Pro Arg Leu Pro Ala Pro Leu
            645                 650                 655

His Leu Ala Asp Arg Leu Val Lys Glu Val Gly Arg Leu Gly Ile Arg
        660                 665                 670

His Leu Lys Glu Val Asp Arg Glu Lys Leu Phe Val
    675                 680                 685

<210> SEQ ID NO 3
<211> LENGTH: 713
<212> TYPE: PRT
<213> ORGANISM: Methanocaldococcus jannaschii

<400> SEQUENCE: 3

Met Val Leu Asn Lys Val Thr Tyr Lys Ile Asn Ala Tyr Lys Ile Lys
1               5                   10                  15

Glu Glu Phe Ile Pro Lys Glu Val His Phe Tyr Arg Ile Lys Ser Phe
            20                  25                  30

Val Asn Glu Ala Phe Asn Phe Tyr Arg Phe Val Asn Phe Gly Gly
        35                  40                  45

Met Ile Ile Asn Lys Lys Asp Lys Ser Phe Val Leu Pro Tyr Lys Val
    50                  55                  60

Asp Asn Lys Val Leu Lys Tyr Lys Asp Gly Asn Asn Glu Ile Pro Ile
65                  70                  75                  80
```

```
Asp Ile Glu Tyr Ile Lys Ser Leu Lys Leu Glu Tyr Val Lys Pro Glu
                85                  90                  95

Ile Ala Glu Lys Leu Val Arg Gly Tyr Leu Lys Ser Val His Lys Ile
            100                 105                 110

Glu Pro Glu Leu Ser Arg Ile Ile Lys Asn Ile Arg Lys His Lys Val
        115                 120                 125

Val Glu Asn Ile Lys Val Glu Ser Tyr Cys Glu Tyr Glu Val Lys Lys
    130                 135                 140

His Asp Gly Asp Tyr Tyr Leu Ile Leu Asn Phe Arg His Thr Ala Ser
145                 150                 155                 160

Ile Thr Lys His Leu Trp Asp Phe Val Asn Arg Asp Lys Ala Leu Leu
                165                 170                 175

Glu Glu Tyr Val Gly Lys Lys Ile Ile Phe Lys Pro Asn Pro Lys Val
            180                 185                 190

Arg Tyr Thr Ile Ser Leu Val Asp Ala Pro Asn Pro Gln Lys Ile Glu
        195                 200                 205

Glu Ile Met Ser His Ile Ile Lys Tyr Tyr Lys Trp Ser Glu Asp Met
    210                 215                 220

Val Lys Ser Thr Phe Gly Glu Ile Asp Tyr Asn Gln Pro Ile Met Tyr
225                 230                 235                 240

Cys Glu Glu Ile Leu Glu Pro Phe Ala Pro Gln Phe Cys Asn Leu Val
                245                 250                 255

Phe Tyr Met Asp Glu Leu Asp Ser Tyr Ile Leu Lys Glu Leu Gln Ser
            260                 265                 270

Tyr Trp Arg Leu Ser Asn Glu Asn Lys Gly Lys Ile Ile Asn Glu Ile
        275                 280                 285

Ala Lys Lys Leu Arg Phe Ile Asp Asn Thr Pro Lys Glu Leu Glu Phe
    290                 295                 300

Met Lys Phe Asn Asn Thr Pro Leu Leu Val Lys Asp Val Asn Lys Asn
305                 310                 315                 320

Pro Thr Lys Ile Tyr Ser Thr Asn Thr Leu Phe Thr Trp Ile Tyr Asn
                325                 330                 335

Gln Asn Ala Lys Ile Tyr Leu Pro Tyr Asp Val Pro Glu Ile Ile Arg
            340                 345                 350

Asn Lys Asn Leu Leu Thr Tyr Ile Leu Ile Asp Glu Glu Ile Lys Asp
        355                 360                 365

Glu Leu Lys Ala Ile Lys Asp Lys Val Asn Lys Met Phe Arg Asn Tyr
    370                 375                 380

Asn Lys Ile Ala Asn Lys Thr Glu Leu Pro Lys Phe Asn Tyr Ala Asn
385                 390                 395                 400

Arg Trp Lys Tyr Phe Ser Thr Asp Asp Ile Arg Gly Ile Ile Lys Glu
                405                 410                 415

Ile Lys Ser Glu Phe Asn Asp Glu Ile Cys Phe Ala Leu Ile Ile Gly
            420                 425                 430

Lys Glu Lys Tyr Lys Asp Asn Asp Tyr Tyr Glu Ile Leu Lys Lys Gln
        435                 440                 445

Leu Phe Asp Leu Lys Ile Ile Ser Gln Asn Ile Leu Trp Glu Asn Trp
    450                 455                 460

Arg Lys Asp Asp Lys Gly Tyr Met Thr Asn Asn Leu Leu Ile Gln Ile
465                 470                 475                 480

Met Gly Lys Leu Gly Ile Lys Tyr Phe Ile Leu Asp Ser Lys Thr Pro
                485                 490                 495
```

```
Tyr Asp Tyr Ile Met Gly Leu Asp Thr Gly Leu Gly Ile Phe Gly Asn
            500                 505                 510

His Arg Val Gly Gly Cys Thr Val Val Tyr Asp Ser Glu Gly Lys Ile
        515                 520                 525

Arg Arg Ile Gln Pro Ile Glu Thr Pro Ala Pro Gly Glu Arg Leu His
    530                 535                 540

Leu Pro Tyr Val Ile Glu Tyr Leu Glu Asn Lys Ala Asn Ile Asp Met
545                 550                 555                 560

Glu Asn Lys Asn Ile Leu Phe Leu Arg Asp Gly Phe Ile Gln Asn Ser
                565                 570                 575

Glu Arg Asn Asp Leu Lys Glu Ile Ser Lys Glu Leu Asn Ser Asn Ile
            580                 585                 590

Glu Val Ile Ser Ile Arg Lys Asn Asn Lys Tyr Lys Val Phe Thr Ser
        595                 600                 605

Asp Tyr Arg Ile Gly Ser Val Phe Gly Asn Asp Gly Ile Phe Leu Pro
    610                 615                 620

His Lys Thr Pro Phe Gly Ser Asn Pro Val Lys Leu Ser Thr Trp Leu
625                 630                 635                 640

Arg Phe Asn Cys Gly Asn Glu Glu Gly Leu Lys Ile Asn Glu Ser Ile
                645                 650                 655

Met Gln Leu Leu Tyr Asp Leu Thr Lys Met Asn Tyr Ser Ala Leu Tyr
            660                 665                 670

Gly Glu Gly Arg Tyr Leu Arg Ile Pro Ala Pro Ile His Tyr Ala Asp
        675                 680                 685

Lys Phe Val Lys Ala Leu Gly Lys Asn Trp Lys Ile Asp Glu Glu Leu
    690                 695                 700

Leu Lys His Gly Phe Leu Tyr Phe Ile
705                 710

<210> SEQ ID NO 4
<211> LENGTH: 639
<212> TYPE: PRT
<213> ORGANISM: Marinitoga piezophila

<400> SEQUENCE: 4

Met Tyr Leu Asn Leu Tyr Lys Ile Asp Ile Pro Lys Lys Ile Lys Arg
1               5                   10                  15

Leu Tyr Phe Tyr Asn Pro Asp Met Glu Pro Lys Leu Phe Ala Arg Asn
            20                  25                  30

Leu Ser Arg Val Asn Asn Phe Lys Phe Gln Asp Ser Asn Asp Leu Val
        35                  40                  45

Trp Ile Glu Ile Pro Asp Ile Asp Phe Gln Ile Thr Pro Lys Asn Val
    50                  55                  60

Phe Gln Tyr Lys Val Glu Lys Glu Ile Ile Lys Glu Glu Asp
65                  70                  75                  80

Lys Lys Leu Phe Val Lys Thr Leu Tyr Lys Tyr Ile Lys Lys Leu Phe
                85                  90                  95

Leu Asp Asn Asp Phe Tyr Phe Lys Lys Gly Asn Asn Phe Ile Ser Asn
            100                 105                 110

Ser Glu Val Phe Ser Leu Asp Ser Asn Glu Asn Val Asn Ala His Leu
        115                 120                 125

Thr Tyr Lys Ile Lys Ile His Asn Ile Ser Asn Glu Tyr Tyr Leu Ser
    130                 135                 140

Ile Leu Pro Lys Phe Thr Phe Leu Ser Lys Glu Pro Ala Leu Glu Ser
145                 150                 155                 160
```

```
Ala Ile Lys Ser Gly Tyr Leu Tyr Asn Ile Lys Ser Gly Lys Ser Phe
            165                 170                 175
Pro Tyr Ile Ser Gly Leu Asp Gly Ile Leu Lys Ile Asp Ile Gly Asn
            180                 185                 190
Asn Gln Ile Val Glu Val Ala Tyr Pro Glu Asn Tyr Leu Phe Asn Phe
            195                 200                 205
Thr Thr Arg Asp Ala Glu Lys Tyr Gly Phe Ser Lys Glu Val His Glu
            210                 215                 220
Ile Tyr Lys Asn Lys Val Phe Glu Gly Phe Lys Lys Ile Pro Lys Thr
225                 230                 235                 240
Leu Gly Phe Leu Asn Lys Ile Thr Asn Leu Asn Glu Asn Tyr Gln Leu
            245                 250                 255
Lys Asp Gly Tyr Lys Ile Phe Ile Asn Val Ile Tyr Lys Phe Lys Asn
            260                 265                 270
Gly Glu Ser Arg Tyr Ala Lys Asp Val Phe Lys Tyr Ser Phe Tyr Lys
            275                 280                 285
Asn Glu Gln Pro Leu Lys Ala Ile Phe Phe Ser Ser Lys Lys Gln
            290                 295                 300
Phe Phe Glu Val Gln Lys Ser Leu Lys Glu Leu Phe His Asn Lys His
305                 310                 315                 320
Ser Val Phe Tyr Arg Ala Ala Ala Glu Leu Gly Phe Ser Lys Val Glu
            325                 330                 335
Phe Leu Arg Asp Ser Lys Thr Lys Ser Ser Ala Phe Leu Tyr Asn Pro
            340                 345                 350
Glu Glu Phe Thr Val Lys Asn Thr Glu Phe Ile Asn Gln Ile Glu Asp
            355                 360                 365
Asn Val Met Ala Ile Val Leu Leu Asp Lys Tyr Ile Gly Asn Ile Asp
            370                 375                 380
Pro Leu Val Arg Asn Phe Pro Asp Asn Leu Ile Leu Gln Pro Ile Leu
385                 390                 395                 400
Lys Glu Lys Leu Glu Asp Ile Lys Pro Phe Ile Ile Lys Ser Tyr Val
            405                 410                 415
Tyr Lys Met Gly Asn Phe Ile Pro Glu Cys Lys Pro Phe Ile Leu Lys
            420                 425                 430
Lys Met Glu Asp Lys Glu Lys Asn Leu Tyr Ile Gly Ile Asp Leu Ser
            435                 440                 445
His Asp Thr Tyr Ala Arg Lys Thr Asn Leu Cys Ile Ala Ala Val Asp
            450                 455                 460
Asn Thr Gly Asp Ile Leu Tyr Ile Gly Lys His Lys Asn Leu Glu Leu
465                 470                 475                 480
Asn Glu Lys Met Asn Leu Asp Ile Leu Glu Lys Glu Tyr Ile Lys Ala
            485                 490                 495
Phe Glu Lys Tyr Ile Glu Lys Phe Asn Val Ser Pro Glu Asn Val Phe
            500                 505                 510
Ile Leu Arg Asp Gly Arg Phe Ile Glu Asp Ile Glu Ile Lys Asn
            515                 520                 525
Phe Ile Ser Tyr Asn Asp Thr Lys Tyr Thr Leu Val Glu Val Asn Lys
            530                 535                 540
Asn Thr Asn Ile Asn Ser Tyr Asp Asp Leu Lys Glu Trp Ile Ile Lys
545                 550                 555                 560
Leu Asp Glu Asn Thr Tyr Ile Tyr Tyr Pro Lys Thr Phe Leu Asn Gln
            565                 570                 575
```

```
Lys Gly Val Glu Val Lys Ile Leu Glu Asn Asn Thr Asp Tyr Thr Ile
                580                 585                 590

Glu Glu Ile Ile Glu Gln Ile Tyr Leu Leu Thr Arg Val Ala His Ser
            595                 600                 605

Thr Pro Tyr Thr Asn Tyr Lys Leu Pro Tyr Pro Leu His Ile Ala Asn
        610                 615                 620

Lys Val Ala Leu Thr Asp Tyr Glu Trp Lys Leu Tyr Ile Pro Tyr
625                 630                 635
```

<210> SEQ ID NO 5
<211> LENGTH: 637
<212> TYPE: PRT
<213> ORGANISM: Thermotoga profunda

<400> SEQUENCE: 5

```
Met Lys Leu Asn Leu Phe Glu Ile Met Val Pro Ser Lys Val Lys Arg
1               5                   10                  15

Ile Tyr Tyr Tyr Asn Pro Gln Thr Pro Pro Glu Ile Phe Ala Lys Asn
            20                  25                  30

Leu Thr Arg Ile Asn Asn Ile Arg Phe Asn Asp Ser Ser Asp Leu Val
        35                  40                  45

Trp Val Glu Leu Pro Phe Leu Gln Val Gln Ile Leu Pro Glu Gln Ala
    50                  55                  60

Val Val Tyr Lys Lys Arg Glu Val Ile Glu Ser Asp Glu Lys Leu
65                  70                  75                  80

Phe Ile Arg Thr Leu Tyr Ser Tyr Ile Lys Lys Leu Phe Lys Asp Asn
                85                  90                  95

Asp Phe Ile Ala Thr Arg Gln Asn Leu Tyr Ile Ser Asn Arg Thr Lys
            100                 105                 110

Thr Pro Phe Gln Asn Asn Lys Glu Val Ser Trp Phe Glu Ser Tyr Gln
        115                 120                 125

Val Lys Ile Tyr Lys Ile Tyr Glu Lys Tyr Tyr Leu Ser Ile Asn Pro
    130                 135                 140

Arg Phe Thr Phe Leu Ser Thr Lys Pro Ala Leu Glu Ser Gln Val Arg
145                 150                 155                 160

Ser Ala Tyr Leu Leu Asn Thr Lys Ser Gly Lys Ser Phe Pro Phe Val
                165                 170                 175

Ser Ala Glu Asp Gly Lys Leu Val Ile Ala Ile Asp Glu Arg Thr His
            180                 185                 190

Lys Glu Val Thr His Pro Glu Asn Tyr Phe Phe Asn Phe Thr Ser Lys
        195                 200                 205

Glu Ala Glu Glu Leu Gly Val Ser Lys Gln Ile Tyr Glu Ile Tyr Asn
    210                 215                 220

Asn Lys Leu Pro Tyr Leu Tyr Glu Lys Ile Ser Thr Glu Leu Ser Phe
225                 230                 235                 240

Leu Lys Asp Leu Val Asn Leu Asn Gln Tyr Tyr Glu Val Lys Pro Asp
                245                 250                 255

His Gln Glu Arg Ile Thr Ala Phe Tyr Lys Phe Ala Asn Gly Asn Ser
            260                 265                 270

Asp Asp Ile Lys Lys Ile Phe Gln Leu Gln Pro Leu Lys Ser Pro Gly
        275                 280                 285

Thr Leu Lys Met Thr Phe Leu Phe Ser Ser Lys Tyr Lys Asn Glu Asn
    290                 295                 300

Ile Ser Glu Pro Val Arg Lys Val Phe Ala Ser Ser Asp Ser Ala Tyr
305                 310                 315                 320
```

```
Arg Lys Ala Leu Ser Glu Leu Gly Leu Glu Ile Glu Tyr Leu Arg Asn
                325                 330                 335

Pro Gln Thr Asn Lys Ala Ile Phe Tyr Tyr Lys Glu Lys Thr Phe Glu
            340                 345                 350

Ile Glu Asn Lys Glu Val Leu Ser Ser Gly Lys Ile Tyr Ala Ile
        355                 360                 365

Val Leu Leu Asp Glu Arg Gln Glu Ser Leu Asp Asn Leu Ile Lys Asn
    370                 375                 380

Ala Pro Lys Asn Val Val Ile Leu Pro Val Leu Thr Pro Lys Ile Ile
385                 390                 395                 400

Ser Asp Gln Ile Tyr Ile Leu Lys Ser Phe Ala Tyr Lys Ile Val Asn
                405                 410                 415

Phe Ser Gln Asp Ala Gln Thr Tyr Gln Leu Leu Gly Leu Ser Asp Asn
            420                 425                 430

Ala Leu Tyr Ile Gly Phe Asp Leu Ser His Asp Phe Gln Lys Arg Val
        435                 440                 445

Ser His Tyr Ala Ile Ser Ala Val Asp Arg Asn Ser Lys Val Leu Tyr
    450                 455                 460

Ile Asn Gln Glu Arg Asp Met Pro Leu Asn Glu Lys Phe Glu Leu Glu
465                 470                 475                 480

Leu Leu Gln Lys Asp Ile Val Lys Ser Ile Asp Arg Tyr Lys Ser Val
                485                 490                 495

Val Lys Lys Pro Pro Asn Met Ile Phe Leu Met Arg Asp Gly Val Phe
            500                 505                 510

Phe Glu Asp Ile Asn Leu Leu Lys Asn Tyr Leu Asp Leu Leu Lys Ile
        515                 520                 525

Asp Tyr Thr Ile Ile Glu Ile Asp Lys Asn Ser Asn Ile Asn Ser Lys
    530                 535                 540

Gln Asn Leu Lys Gly Met Ile Val Lys Phe Glu Pro Asn Lys Tyr Val
545                 550                 555                 560

Tyr Phe Ala Gln Thr Tyr Asn Leu Gln Lys Ala Val Glu Ile Asn Ile
                565                 570                 575

Val Ile Asn Asn Ser Lys Leu Ser Asp Glu Gln Ile Ala Arg Glu Thr
            580                 585                 590

Tyr Leu Thr Thr Arg Leu Phe His Ser Thr Pro Tyr Thr Asn Leu Lys
        595                 600                 605

Leu Pro Tyr Pro Leu Tyr Ile Thr Asp Lys Val Ala Leu Leu Asn Asn
    610                 615                 620

Glu Trp Lys Leu Tyr Ile Pro Tyr Phe Cys Asp Lys Ile
625                 630                 635

<210> SEQ ID NO 6
<211> LENGTH: 777
<212> TYPE: PRT
<213> ORGANISM: Rhodobacter sphaeroides

<400> SEQUENCE: 6

Met Ala Pro Val Gln Ala Ala Asp Glu Met Tyr Asp Ser Asn Pro His
1               5                   10                  15

Pro Asp Arg Arg Gln Leu Val Ser Asn Gly Phe Glu Val Asn Leu Pro
            20                  25                  30

Asp Gln Val Glu Val Ile Val Arg Asp Leu Pro Asp Pro Ser Lys Val
        35                  40                  45

Lys Glu Glu Arg Thr Arg Leu Met Gly Tyr Trp Phe Val His Trp Phe
```

```
              50                  55                  60
Asp Gly Lys Leu Phe His Leu Arg Ile Lys Ala Gly Pro Asn Val
 65                      70                  75                  80

Asp Gly Glu His Arg Ala Ile Arg Thr Ala Glu His Pro Trp Leu Leu
                     85                  90                  95

Arg Ala Arg Leu Asp Asp Ala Leu Glu Ala Leu Pro Lys Tyr Ala
                100                 105                 110

Ala Val Lys Lys Arg Pro Phe Thr Phe Leu Ala Gln Lys Asp Glu Leu
                115                 120                 125

Ile Asp Ala Ala Ala Thr Ala Ala Gly Leu Ser His Arg Leu Leu Asn
130                 135                 140

Ser Phe Lys Val Ile Pro Arg Phe Ala Leu Ser Pro Lys Ile Tyr Glu
145                 150                 155                 160

Pro Val Asp Gly Thr Thr Arg Val Gly Val Phe Val Thr Ile Gly Met
                165                 170                 175

Arg Tyr Asp Ile Glu Ala Ser Leu Arg Asp Leu Leu Glu Ala Gly Ile
                180                 185                 190

Asp Leu Arg Gly Met Tyr Val Val Arg Arg Lys Arg Gln Pro Gly Glu
                195                 200                 205

Arg Gly Leu Leu Gly Arg Val Arg Ala Ile Ser Asp Asp Met Val Gln
210                 215                 220

Leu Phe Glu Glu Thr Asp Leu Ala Ser Val Asn Val Asn Asp Ala Lys
225                 230                 235                 240

Leu Glu Gly Ser Lys Glu Asn Phe Thr Arg Cys Leu Ser Ala Leu Leu
                245                 250                 255

Gly His Asn Tyr Lys Lys Leu Leu Asn Ala Leu Asp Asp Gln Glu Ala
                260                 265                 270

Gly Tyr Arg Thr Gly Pro Arg Phe Asp Asp Ala Val Arg Met Gly
                275                 280                 285

Glu Phe Leu Ala Lys Lys Pro Ile Arg Leu Ala Asp Asn Ile Asn Ala
290                 295                 300

Gln Val Gly Asp Arg Ile Val Phe Ser Asn Glu Gly Gln Ala Arg Asn
305                 310                 315                 320

Val Arg Leu Ala Pro Lys Val Glu Tyr Val Phe Asp Arg Thr Gly Ala
                325                 330                 335

Lys Ser Ala Glu Tyr Ala Trp Arg Gly Leu Ser Gln Phe Gly Pro Phe
                340                 345                 350

Asp Arg Pro Ser Phe Ala Asn Arg Ser Pro Arg Ile Leu Val Val Tyr
                355                 360                 365

Pro Ser Ser Thr Gln Gly Lys Val Glu Asn Phe Leu Ser Ala Phe Arg
                370                 375                 380

Asp Gly Met Gly Ser Asn Tyr Ser Gly Phe Ser Lys Gly Phe Val Asp
385                 390                 395                 400

Leu Met Gly Leu Thr Lys Val Glu Phe Val Met Cys Pro Val Glu Val
                405                 410                 415

Ser Ser Ala Asp Arg Asn Gly Ala His Thr Lys Tyr Asn Ser Ala Ile
                420                 425                 430

Glu Asp Lys Leu Ala Gly Ala Gly Glu Val His Ala Gly Ile Val Val
                435                 440                 445

Leu Phe Glu Asp His Ala Arg Leu Pro Asp Asp Arg Asn Pro Tyr Ile
                450                 455                 460

His Thr Lys Ser Leu Leu Leu Thr Leu Gly Val Pro Thr Gln Gln Val
465                 470                 475                 480
```

```
Arg Met Pro Thr Val Leu Leu Glu Pro Lys Ser Leu Gln Tyr Thr Leu
                485                 490                 495

Gln Asn Phe Ser Ile Ala Thr Tyr Ala Lys Leu Asn Gly Thr Pro Trp
            500                 505                 510

Thr Val Asn His Asp Lys Ala Ile Asn Asp Glu Leu Val Val Gly Met
        515                 520                 525

Gly Leu Ala Glu Leu Ser Gly Ser Arg Thr Glu Lys Arg Gln Arg Phe
    530                 535                 540

Val Gly Ile Thr Thr Val Phe Ala Gly Asp Gly Ser Tyr Leu Leu Gly
545                 550                 555                 560

Asn Val Ser Lys Glu Cys Glu Tyr Glu Gly Tyr Ser Asp Ala Ile Arg
                565                 570                 575

Glu Ser Met Thr Gly Ile Leu Arg Glu Leu Lys Lys Arg Asn Asn Trp
            580                 585                 590

Arg Pro Gly Asp Thr Val Arg Val Phe His Ala His Arg Pro Leu
        595                 600                 605

Lys Arg Val Asp Val Ala Ser Ile Val Phe Glu Cys Thr Arg Glu Ile
    610                 615                 620

Gly Ser Asp Gln Asn Ile Gln Met Ala Phe Val Thr Val Ser His Asp
625                 630                 635                 640

His Pro Phe Val Leu Ile Asp Arg Ser Glu Arg Gly Leu Glu Ala Tyr
                645                 650                 655

Lys Gly Ser Thr Ala Arg Lys Gly Val Phe Ala Pro Pro Arg Gly Ala
            660                 665                 670

Ile Ser Arg Val Gly Arg Leu Thr Arg Leu Leu Ala Val Asn Ser Pro
        675                 680                 685

Gln Leu Ile Lys Arg Ala Asn Thr Pro Leu Pro Thr Pro Leu Leu Val
    690                 695                 700

Ser Leu His Pro Asp Ser Thr Phe Lys Asp Val Asp Tyr Leu Ala Glu
705                 710                 715                 720

Gln Ala Leu Lys Phe Thr Ser Leu Ser Trp Arg Ser Thr Leu Pro Ala
                725                 730                 735

Ala Thr Pro Val Thr Ile Phe Tyr Ser Glu Arg Ile Ala Glu Leu Leu
            740                 745                 750

Gly Arg Leu Lys Ser Ile Pro Asn Trp Ser Ser Ala Asn Leu Asn Ile
        755                 760                 765

Lys Leu Lys Trp Ser Arg Trp Phe Leu
    770                 775

<210> SEQ ID NO 7
<211> LENGTH: 706
<212> TYPE: PRT
<213> ORGANISM: Aquifex aeolicus

<400> SEQUENCE: 7

Met Gly Lys Glu Ala Leu Leu Asn Leu Tyr Arg Ile Glu Tyr Arg Pro
1               5                   10                  15

Lys Asp Thr Thr Phe Thr Val Phe Lys Pro Thr His Glu Ile Gln Lys
            20                  25                  30

Glu Lys Leu Asn Lys Val Arg Trp Arg Val Phe Leu Gln Thr Gly Leu
        35                  40                  45

Pro Thr Phe Arg Arg Glu Asp Glu Phe Trp Cys Ala Gly Lys Val Glu
    50                  55                  60

Lys Asp Thr Leu Tyr Leu Thr Leu Ser Asn Gly Glu Ile Val Glu Leu
```

```
            65                  70                  75                  80
Lys Arg Val Gly Glu Glu Phe Arg Gly Phe Gln Asn Glu Arg Glu
                    85                  90                  95
Cys Gln Glu Leu Phe Arg Asp Phe Leu Thr Lys Thr Lys Val Lys Asp
                100                 105                 110
Lys Phe Ile Ser Asp Phe Tyr Lys Phe Arg Asp Lys Ile Thr Val
                115                 120                 125
Gln Gly Lys Asn Arg Lys Ile Ala Leu Ile Pro Glu Val Asn Glu Lys
130                 135                 140
Val Leu Lys Ser Glu Glu Gly Tyr Phe Leu Leu His Leu Asp Leu Lys
145                 150                 155                 160
Phe Arg Ile Gln Pro Phe Glu Thr Leu Gln Thr Leu Leu Glu Arg Asn
                165                 170                 175
Asp Phe Asn Pro Lys Arg Ile Arg Val Lys Pro Ile Gly Ile Asp Phe
                180                 185                 190
Val Gly Arg Val Gln Asp Val Phe Lys Ala Lys Glu Lys Gly Glu Glu
                195                 200                 205
Phe Phe Arg Leu Cys Met Glu Arg Ser Thr His Lys Ser Ser Lys Lys
            210                 215                 220
Ala Trp Glu Glu Leu Leu Lys Asn Arg Glu Leu Arg Glu Lys Ala Phe
225                 230                 235                 240
Leu Val Val Leu Glu Lys Gly Tyr Thr Tyr Pro Ala Thr Ile Leu Lys
                245                 250                 255
Pro Val Leu Thr Tyr Glu Asn Leu Glu Asp Glu Glu Arg Asn Glu Val
                260                 265                 270
Ala Asp Ile Val Arg Met Glu Pro Gly Lys Arg Leu Asn Leu Ile Arg
            275                 280                 285
Tyr Ile Leu Arg Arg Tyr Val Lys Ala Leu Arg Asp Tyr Gly Trp Tyr
            290                 295                 300
Ile Ser Pro Glu Glu Arg Ala Lys Gly Lys Leu Asn Phe Lys Asp
305                 310                 315                 320
Thr Val Leu Asp Ala Lys Gly Lys Asn Thr Lys Val Ile Thr Asn Leu
                325                 330                 335
Arg Lys Phe Leu Glu Leu Cys Arg Pro Phe Val Lys Asp Val Leu
                340                 345                 350
Ser Val Glu Ile Ile Ser Val Ser Val Tyr Lys Lys Leu Glu Trp Arg
            355                 360                 365
Lys Glu Glu Phe Leu Lys Glu Leu Ile Asn Phe Leu Lys Asn Lys Gly
            370                 375                 380
Ile Lys Leu Lys Ile Lys Gly Lys Ser Leu Ile Leu Ala Gln Thr Arg
385                 390                 395                 400
Glu Glu Ala Lys Glu Lys Leu Ile Pro Val Ile Asn Lys Ile Lys Asp
                405                 410                 415
Val Asp Leu Val Ile Val Phe Leu Glu Glu Tyr Pro Lys Val Asp Pro
                420                 425                 430
Tyr Lys Ser Phe Leu Leu Tyr Asp Phe Val Lys Arg Glu Leu Leu Lys
            435                 440                 445
Lys Met Ile Pro Ser Gln Val Ile Leu Asn Arg Thr Leu Lys Asn Glu
            450                 455                 460
Asn Leu Lys Phe Val Leu Leu Asn Val Ala Glu Gln Val Leu Ala Lys
465                 470                 475                 480
Thr Gly Asn Ile Pro Tyr Lys Leu Lys Glu Ile Glu Gly Lys Val Asp
                485                 490                 495
```

```
Ala Phe Val Gly Ile Asp Ile Ser Arg Ile Thr Arg Asp Gly Lys Thr
            500                 505                 510

Val Asn Ala Val Ala Phe Thr Lys Ile Phe Asn Ser Lys Gly Glu Leu
            515                 520                 525

Val Arg Tyr Tyr Leu Thr Ser Tyr Pro Ala Phe Gly Glu Lys Leu Thr
530                 535                 540

Glu Lys Ala Ile Gly Asp Val Phe Ser Leu Leu Glu Lys Leu Gly Phe
545                 550                 555                 560

Lys Lys Gly Ser Lys Ile Val His Arg Asp Gly Arg Leu Tyr Arg
                565                 570                 575

Asp Glu Val Ala Ala Phe Lys Lys Tyr Gly Glu Leu Tyr Gly Tyr Ser
            580                 585                 590

Leu Glu Leu Leu Glu Ile Ile Lys Arg Asn Asn Pro Arg Phe Phe Ser
        595                 600                 605

Asn Glu Lys Phe Ile Lys Gly Tyr Phe Tyr Lys Leu Ser Glu Asp Ser
        610                 615                 620

Val Ile Leu Ala Thr Tyr Asn Gln Val Tyr Glu Gly Thr His Gln Pro
625                 630                 635                 640

Ile Lys Val Arg Lys Val Tyr Gly Glu Leu Pro Val Glu Val Leu Cys
                645                 650                 655

Ser Gln Ile Leu Ser Leu Thr Leu Met Asn Tyr Ser Ser Phe Gln Pro
            660                 665                 670

Ile Lys Leu Pro Ala Thr Val His Tyr Ser Asp Lys Ile Thr Lys Leu
        675                 680                 685

Met Leu Arg Gly Ile Glu Pro Ile Lys Lys Glu Gly Asp Ile Met Tyr
        690                 695                 700

Trp Leu
705

<210> SEQ ID NO 8
<211> LENGTH: 427
<212> TYPE: PRT
<213> ORGANISM: Archaeoglobus fulgidus

<400> SEQUENCE: 8

Met Met Glu Tyr Lys Ile Val Glu Asn Gly Leu Thr Tyr Arg Ile Gly
1               5                   10                  15

Asn Gly Ala Ser Val Pro Ile Ser Asn Thr Gly Glu Leu Ile Lys Gly
            20                  25                  30

Leu Arg Asn Tyr Gly Pro Tyr Glu Val Pro Ser Leu Lys Tyr Asn Gln
        35                  40                  45

Ile Ala Leu Ile His Asn Asn Gln Phe Ser Ser Leu Ile Asn Gln Leu
    50                  55                  60

Lys Ser Gln Ile Ser Ser Lys Ile Asp Glu Val Trp His Ile His Asn
65                  70                  75                  80

Ile Asn Ile Ser Glu Phe Ile Tyr Asp Ser Pro His Phe Asp Ser Ile
                85                  90                  95

Lys Ser Gln Val Asp Asn Ala Ile Asp Thr Gly Val Asp Gly Ile Met
            100                 105                 110

Leu Val Leu Pro Glu Tyr Asn Thr Pro Leu Tyr Tyr Lys Leu Lys Ser
        115                 120                 125

Tyr Leu Ile Asn Ser Ile Pro Ser Gln Phe Met Arg Tyr Asp Ile Leu
    130                 135                 140

Ser Asn Arg Asn Leu Thr Phe Tyr Val Asp Asn Leu Leu Val Gln Phe
```

```
                145                 150                 155                 160
    Val Ser Lys Leu Gly Lys Pro Trp Ile Leu Asn Val Asp Pro Glu
                    165                 170                 175

Lys Gly Ser Asp Ile Ile Ile Gly Thr Gly Ala Thr Arg Ile Asp Asn
                    180                 185                 190

Val Asn Leu Phe Cys Phe Ala Met Val Phe Lys Lys Asp Gly Thr Met
                    195                 200                 205

Leu Trp Asn Glu Ile Ser Pro Ile Val Thr Ser Glu Tyr Leu Thr
            210                 215                 220

Tyr Leu Lys Ser Thr Ile Lys Lys Val Val Tyr Gly Phe Lys Lys Ser
    225                 230                 235                 240

Asn Pro Asp Trp Asp Val Glu Lys Leu Thr Leu His Val Ser Gly Lys
                    245                 250                 255

Arg Pro Lys Met Lys Asp Gly Glu Thr Lys Ile Leu Lys Glu Thr Val
                    260                 265                 270

Glu Glu Leu Lys Lys Gln Glu Met Val Ser Arg Asp Val Lys Tyr Ala
                    275                 280                 285

Ile Leu His Leu Asn Glu Thr His Pro Phe Trp Val Met Gly Asp Pro
            290                 295                 300

Asn Asn Arg Phe His Pro Tyr Glu Gly Thr Lys Val Lys Leu Ser Ser
    305                 310                 315                 320

Lys Arg Tyr Leu Leu Thr Leu Leu Gln Pro Tyr Leu Lys Arg Asn Gly
                    325                 330                 335

Leu Glu Met Val Thr Pro Ile Lys Pro Leu Ser Val Glu Ile Val Ser
                    340                 345                 350

Asp Asn Trp Thr Ser Glu Glu Tyr Tyr His Asn Val His Glu Ile Leu
                    355                 360                 365

Asp Glu Ile Tyr Tyr Leu Ser Lys Met Asn Trp Arg Gly Phe Arg Ser
            370                 375                 380

Arg Asn Leu Pro Val Thr Val Asn Tyr Pro Lys Leu Val Ala Gly Ile
    385                 390                 395                 400

Ile Ala Asn Val Asn Arg Tyr Gly Gly Tyr Pro Ile Asn Pro Glu Gly
                    405                 410                 415

Asn Arg Ser Leu Gln Thr Asn Pro Trp Phe Leu
                    420                 425

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gDNA

<400> SEQUENCE: 9
ctcccaacca agctctcttg                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gDNA
```

```
<400> SEQUENCE: 10
tagggactct ggatcccaga                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gDNA

<400> SEQUENCE: 11
tgaggcagat gcccagcagg                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gDNA

<400> SEQUENCE: 12
tctgtgatct tgacatgctg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taatacgact cactataggg                                               20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctagttatt gctcagcgg                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatgatacgg cgaccaccga                                               20

<210> SEQ ID NO 16
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 16
caagcagaag acggcatacg agat                                          24

<210> SEQ ID NO 17
<211> LENGTH: 11
<212> TYPE: PRT
<213> ORGANISM: Homo sapiens

<400> SEQUENCE: 17

Ile Phe Leu Gly Ala Asp Val Thr His Pro Pro
1               5                   10

<210> SEQ ID NO 18
<211> LENGTH: 10
<212> TYPE: PRT
<213> ORGANISM: Homo sapiens

<400> SEQUENCE: 18

Gln His Arg Gln Glu Ile Ile Gln Asp Leu
1               5                   10

<210> SEQ ID NO 19
<211> LENGTH: 11
<212> TYPE: PRT
<213> ORGANISM: Homo sapiens

<400> SEQUENCE: 19

Ile Ile Phe Tyr Arg Asp Gly Val Ser Glu Gly
1               5                   10

<210> SEQ ID NO 20
<211> LENGTH: 11
<212> TYPE: PRT
<213> ORGANISM: Homo sapiens

<400> SEQUENCE: 20

Pro Ala Tyr Tyr Ala His Leu Val Ala Phe Arg
1               5                   10

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
attggaattg atgttgctcc c                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
attggaattg ctgttgctcc c                                             21

<210> SEQ ID NO 23
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cttctaagag atggaagaat t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cttctaagag ctggaagaat t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cttctaagat gaggatcccg g                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
caaagaggag aatcagttga c                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caaagaggag catcagttga c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cactatgctc acaagtttgc a                                              21

<210> SEQ ID NO 29
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cactatgctg ccaagtttgc a                                              21

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5

<210> SEQ ID NO 31
<211> LENGTH: 11
<212> TYPE: PRT
<213> ORGANISM: Thermus thermophilus

<400> SEQUENCE: 31

Leu Ala Val Gly Phe Asp Ala Gly Gly Arg Glu
1               5                   10

<210> SEQ ID NO 32
<211> LENGTH: 9
<212> TYPE: PRT
<213> ORGANISM: Thermus thermophilus

<400> SEQUENCE: 32

Gly Glu Arg Ile Pro Gln Glu Val Val
1               5

<210> SEQ ID NO 33
<211> LENGTH: 9
<212> TYPE: PRT
<213> ORGANISM: Thermus thermophilus

<400> SEQUENCE: 33

Val Leu Leu Leu Arg Asp Gly Arg Val
1               5

<210> SEQ ID NO 34
<211> LENGTH: 11
<212> TYPE: PRT
<213> ORGANISM: Thermus thermophilus

<400> SEQUENCE: 34

Pro Leu His Leu Ala Asp Arg Leu Val Lys Glu
1               5                   10

<210> SEQ ID NO 35
<211> LENGTH: 11
<212> TYPE: PRT
<213> ORGANISM: Methanocaldococcus jannaschii

<400> SEQUENCE: 35

Tyr Ile Met Gly Leu Asp Thr Gly Leu Gly Ile
1               5                   10
```

```
<210> SEQ ID NO 36
<211> LENGTH: 9
<212> TYPE: PRT
<213> ORGANISM: Methanocaldococcus jannaschii

<400> SEQUENCE: 36

Gly Glu Arg Leu His Leu Pro Tyr Val
1               5

<210> SEQ ID NO 37
<211> LENGTH: 9
<212> TYPE: PRT
<213> ORGANISM: Methanocaldococcus jannaschii

<400> SEQUENCE: 37

Ile Leu Phe Leu Arg Asp Gly Phe Ile
1               5

<210> SEQ ID NO 38
<211> LENGTH: 11
<212> TYPE: PRT
<213> ORGANISM: Methanocaldococcus jannaschii

<400> SEQUENCE: 38

Pro Ile His Tyr Ala Asp Lys Phe Val Lys Ala
1               5                   10

<210> SEQ ID NO 39
<211> LENGTH: 11
<212> TYPE: PRT
<213> ORGANISM: Pyrococcus furiosus

<400> SEQUENCE: 39

Tyr Ile Ile Gly Ile Asp Val Ala Pro Met Lys
1               5                   10

<210> SEQ ID NO 40
<211> LENGTH: 10
<212> TYPE: PRT
<213> ORGANISM: Pyrococcus furiosus

<400> SEQUENCE: 40

Gly Glu Gln Arg Gly Glu Ser Val Asp Met
1               5                   10

<210> SEQ ID NO 41
<211> LENGTH: 9
<212> TYPE: PRT
<213> ORGANISM: Pyrococcus furiosus

<400> SEQUENCE: 41

Ile Leu Leu Leu Arg Asp Gly Arg Ile
1               5

<210> SEQ ID NO 42
<211> LENGTH: 11
<212> TYPE: PRT
<213> ORGANISM: Pyrococcus furiosus

<400> SEQUENCE: 42

Pro Val His Tyr Ala His Lys Phe Ala Asn Ala
1               5                   10

<210> SEQ ID NO 43
```

```
<211> LENGTH: 11
<212> TYPE: PRT
<213> ORGANISM: Marinitoga piezophila

<400> SEQUENCE: 43

Leu Tyr Ile Gly Ile Asp Leu Ser His Asp Thr
1               5                   10

<210> SEQ ID NO 44
<211> LENGTH: 9
<212> TYPE: PRT
<213> ORGANISM: Marinitoga piezophila

<400> SEQUENCE: 44

Asn Glu Lys Met Asn Leu Asp Ile Leu
1               5

<210> SEQ ID NO 45
<211> LENGTH: 11
<212> TYPE: PRT
<213> ORGANISM: Marinitoga piezophila

<400> SEQUENCE: 45

Val Phe Ile Leu Arg Asp Gly Arg Phe Ile Glu
1               5                   10

<210> SEQ ID NO 46
<211> LENGTH: 11
<212> TYPE: PRT
<213> ORGANISM: Marinitoga piezophila

<400> SEQUENCE: 46

Pro Leu His Ile Ala Asn Lys Val Ala Leu Thr
1               5                   10

<210> SEQ ID NO 47
<211> LENGTH: 11
<212> TYPE: PRT
<213> ORGANISM: Thermotoga profunda

<400> SEQUENCE: 47

Leu Tyr Ile Gly Phe Asp Leu Ser His Asp Phe
1               5                   10

<210> SEQ ID NO 48
<211> LENGTH: 9
<212> TYPE: PRT
<213> ORGANISM: Thermotoga profunda

<400> SEQUENCE: 48

Asn Glu Lys Phe Glu Leu Glu Leu Leu
1               5

<210> SEQ ID NO 49
<211> LENGTH: 11
<212> TYPE: PRT
<213> ORGANISM: Thermotoga profunda

<400> SEQUENCE: 49

Ile Phe Leu Met Arg Asp Gly Val Phe Phe Glu
1               5                   10

<210> SEQ ID NO 50
<211> LENGTH: 11
<212> TYPE: PRT
```

```
<213> ORGANISM: Thermotoga profunda

<400> SEQUENCE: 50

Pro Leu Tyr Ile Thr Asp Lys Val Ala Leu Leu
1               5                   10

<210> SEQ ID NO 51
<211> LENGTH: 11
<212> TYPE: PRT
<213> ORGANISM: Aquifex aeolicus

<400> SEQUENCE: 51

Ala Phe Val Gly Ile Asp Ile Ser Arg Ile Thr
1               5                   10

<210> SEQ ID NO 52
<211> LENGTH: 9
<212> TYPE: PRT
<213> ORGANISM: Aquifex aeolicus

<400> SEQUENCE: 52

Asn Glu Asn Leu Lys Phe Val Leu Leu
1               5

<210> SEQ ID NO 53
<211> LENGTH: 11
<212> TYPE: PRT
<213> ORGANISM: Aquifex aeolicus

<400> SEQUENCE: 53

Ile Val Val His Arg Asp Gly Arg Leu Tyr Arg
1               5                   10

<210> SEQ ID NO 54
<211> LENGTH: 11
<212> TYPE: PRT
<213> ORGANISM: Aquifex aeolicus

<400> SEQUENCE: 54

Thr Val His Tyr Ser Asp Lys Ile Thr Lys Leu
1               5                   10

<210> SEQ ID NO 55
<211> LENGTH: 11
<212> TYPE: PRT
<213> ORGANISM: Archaeoglobus fulgidus

<400> SEQUENCE: 55

Trp Ile Leu Asn Val Asp Pro Glu Lys Gly Ser
1               5                   10

<210> SEQ ID NO 56
<211> LENGTH: 9
<212> TYPE: PRT
<213> ORGANISM: Archaeoglobus fulgidus

<400> SEQUENCE: 56

Ser Gln Phe Met Arg Tyr Asp Ile Leu
1               5

<210> SEQ ID NO 57
<211> LENGTH: 11
<212> TYPE: PRT
<213> ORGANISM: Archaeoglobus fulgidus
```

```
<400> SEQUENCE: 57

Met Val Phe Lys Lys Asp Gly Thr Met Leu Trp
1               5                   10

<210> SEQ ID NO 58
<211> LENGTH: 11
<212> TYPE: PRT
<213> ORGANISM: Archaeoglobus fulgidus

<400> SEQUENCE: 58

Pro Leu Tyr Tyr Lys Leu Lys Ser Tyr Leu Ile
1               5                   10

<210> SEQ ID NO 59
<211> LENGTH: 11
<212> TYPE: PRT
<213> ORGANISM: Rhodobacter sphaeroides

<400> SEQUENCE: 59

Leu Val Val Gly Met Gly Leu Ala Glu Leu Ser
1               5                   10

<210> SEQ ID NO 60
<211> LENGTH: 9
<212> TYPE: PRT
<213> ORGANISM: Rhodobacter sphaeroides

<400> SEQUENCE: 60

Asn Thr Pro Leu Pro Thr Pro Leu Leu
1               5

<210> SEQ ID NO 61
<211> LENGTH: 11
<212> TYPE: PRT
<213> ORGANISM: Rhodobacter sphaeroides

<400> SEQUENCE: 61

Thr Val Phe Ala Gly Asp Gly Ser Tyr Leu Leu
1               5                   10

<210> SEQ ID NO 62
<211> LENGTH: 11
<212> TYPE: PRT
<213> ORGANISM: Rhodobacter sphaeroides

<400> SEQUENCE: 62

Asn Pro Tyr Ile His Thr Lys Ser Leu Leu Leu
1               5                   10
```